(12) United States Patent
Goldblum et al.

(10) Patent No.: US 8,653,041 B2
(45) Date of Patent: *Feb. 18, 2014

(54) ANTIBACTERIAL AMINOGLYCOSIDE ANALOGS

(71) Applicant: Achaogen, Inc., South San Francisco, CA (US)

(72) Inventors: Adam Aaron Goldblum, Berkeley, CA (US); Paola Dozzo, San Francisco, CA (US); Timothy Robert Kane, Moss Beach, CA (US); James Bradley Aggen, Burlingame, CA (US); Martin Sheringham Linsell, San Mateo, CA (US); Darin James Hildebrandt, Cupertino, CA (US); Micah James Gliedt, Sunnyvale, CA (US)

(73) Assignee: Achaogen, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/652,163

(22) Filed: Oct. 15, 2012

(65) Prior Publication Data

US 2013/0178438 A1 Jul. 11, 2013

Related U.S. Application Data

(63) Continuation of application No. 13/295,219, filed on Nov. 14, 2011, now Pat. No. 8,318,685.

(60) Provisional application No. 61/505,371, filed on Jul. 7, 2011, provisional application No. 61/414,762, filed on Nov. 17, 2010.

(51) Int. Cl.
*A61K 31/70* (2006.01)

(52) U.S. Cl.
USPC .................. 514/38; 514/27; 514/35; 514/36; 514/39; 514/40

(58) Field of Classification Search
None
See application file for complete search history.

(56) References Cited

U.S. PATENT DOCUMENTS

| | | | |
|---|---|---|---|
| 3,808,198 | A | 4/1974 | Naito et al. |
| 3,860,574 | A | 1/1975 | Naito et al. |
| 3,896,106 | A | 7/1975 | Naito et al. |
| 3,897,412 | A | 7/1975 | Naito et al. |
| 3,956,274 | A | 5/1976 | Umezawa et al. |
| 4,021,601 | A | 5/1977 | Arcamone et al. |
| 4,066,753 | A | 1/1978 | Hanessian |
| 4,078,138 | A | 3/1978 | Akita et al. |
| 4,170,642 | A | 10/1979 | Umezawa et al. |
| 4,247,687 | A | 1/1981 | Hanessian |
| 4,337,248 | A | 6/1982 | Battistini et al. |
| 4,347,354 | A | 8/1982 | Cron et al. |
| 4,424,343 | A | 1/1984 | Cron et al. |
| 4,617,293 | A | 10/1986 | Wahlig et al. |
| 4,937,257 | A | 6/1990 | Gericke et al. |
| 5,470,836 | A | 11/1995 | Donno et al. |
| 5,534,408 | A | 7/1996 | Green et al. |
| 5,763,587 | A | 6/1998 | Mangia |
| 5,935,776 | A | 8/1999 | Green et al. |
| 5,942,547 | A | 8/1999 | Gustafson et al. |
| 6,140,361 | A | 10/2000 | Gustafson et al. |
| 6,541,456 | B1 | 4/2003 | Swayze et al. |
| 6,759,523 | B2 | 7/2004 | Swayze et al. |
| 6,967,242 | B2 | 11/2005 | Swayze et al. |

(Continued)

FOREIGN PATENT DOCUMENTS

| | | |
|---|---|---|
| CA | 1 271 744 | 7/1990 |
| DE | 25 15 629 A1 | 10/1975 |

(Continued)

OTHER PUBLICATIONS

Alper et al., "Metal Catalyzed Diazo Transfer for the Synthesis of Azides From Amines," *Tetrahedron Letters* 37(34):6029-6032, 1996.
Alper et al., "Probing the Specificity of Aminoglycoside-Ribosomal RNA Interactions with Designed Synthetic Analogs," *J. Am. Chem. Soc.* 120(9):1965-1978, 1998.
Banker, G.S., et al., "*Modern Pharmceutics, Third Edition, Revised and Expanded*," Marcel Dekker, Inc., New York, 596, 1996.
Battistini et al., "Semisynthetic Aminoglycoside Antibiotics. IV 3',4'-Dideoxyparomomycin and Analogues," *The Journal of Antibiotics* 35(1):98-101, Jan. 1982.

(Continued)

*Primary Examiner* — Traviss C McIntosh, III
(74) *Attorney, Agent, or Firm* — Cooley LLP

(57) ABSTRACT

Compounds having antibacterial activity are disclosed. The compounds have the following structure (I):

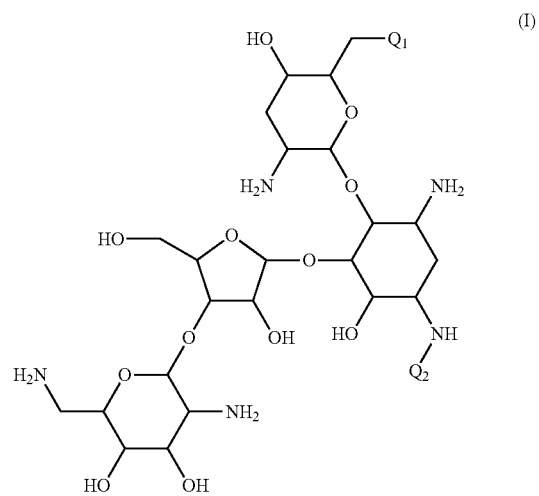

including stereoisomers, prodrugs and pharmaceutically acceptable salts thereof, wherein $Q_1$ and $Q_2$ are as defined herein. Methods associated with preparation and use of such compounds, as well as pharmaceutical compositions comprising such compounds, are also disclosed.

20 Claims, No Drawings

(56) References Cited

U.S. PATENT DOCUMENTS

| | | | |
|---|---|---|---|
| 7,893,039 B2 | 2/2011 | Swayze et al. | |
| 8,114,856 B2 | 2/2012 | Swayze et al. | |
| 8,318,685 B2 * | 11/2012 | Goldblum et al. | 514/38 |
| 8,367,625 B2 | 2/2013 | Aggen et al. | |
| 8,372,813 B2 | 2/2013 | Aggen et al. | |
| 8,377,896 B2 | 2/2013 | Migawa et al. | |
| 8,383,596 B2 | 2/2013 | Aggen et al. | |
| 8,399,419 B2 | 3/2013 | Aggen et al. | |
| 8,481,502 B2 | 7/2013 | Aggen et al. | |
| 8,492,354 B2 | 7/2013 | Dozzo et al. | |
| 8,524,675 B2 | 9/2013 | Dozzo et al. | |
| 8,524,689 B2 | 9/2013 | Goldblum et al. | |
| 2004/0229265 A1 | 11/2004 | Lapidot et al. | |
| 2005/0004052 A1 | 1/2005 | Baasov et al. | |
| 2005/0148522 A1 | 7/2005 | Baasov et al. | |
| 2008/0045468 A1 | 2/2008 | Hanessian et al. | |
| 2008/0214845 A1 | 9/2008 | Migawa et al. | |
| 2008/0293649 A1 | 11/2008 | Swayze et al. | |
| 2008/0300199 A1 * | 12/2008 | Linsell et al. | 514/38 |
| 2010/0099661 A1 | 4/2010 | Aggen et al. | |
| 2011/0166334 A1 | 7/2011 | Swayze et al. | |
| 2011/0245476 A1 | 10/2011 | Migawa et al. | |
| 2011/0275586 A1 | 11/2011 | Aggen et al. | |
| 2011/0288041 A1 | 11/2011 | Aggen et al. | |
| 2012/0122809 A1 | 5/2012 | Goldblum et al. | |
| 2012/0135945 A1 | 5/2012 | Dozzo et al. | |
| 2012/0135946 A1 | 5/2012 | Goldblum et al. | |
| 2012/0135948 A1 | 5/2012 | Goldblum et al. | |
| 2012/0165282 A1 | 6/2012 | Dozzo et al. | |
| 2012/0172332 A1 | 7/2012 | Aggen et al. | |
| 2012/0184501 A1 | 7/2012 | Dozzo et al. | |
| 2012/0196791 A1 | 8/2012 | Armstrong et al. | |
| 2012/0208781 A1 | 8/2012 | Bruss et al. | |
| 2012/0214759 A1 | 8/2012 | Bruss et al. | |
| 2012/0214760 A1 | 8/2012 | Bruss et al. | |
| 2012/0258925 A1 | 10/2012 | Aggen et al. | |
| 2012/0283207 A1 | 11/2012 | Maianti et al. | |
| 2012/0283208 A1 | 11/2012 | Aggen et al. | |
| 2012/0283209 A1 | 11/2012 | Dozzo et al. | |
| 2013/0005674 A1 | 1/2013 | Swayze et al. | |
| 2013/0144044 A1 | 6/2013 | Migawa et al. | |
| 2013/0217642 A1 | 8/2013 | Aggen et al. | |

FOREIGN PATENT DOCUMENTS

| | | |
|---|---|---|
| DE | 29 36 120 A1 | 3/1980 |
| DE | 30 44 970 A1 | 9/1981 |
| DE | 34 05 326 A1 | 8/1985 |
| EP | 0 021 150 A1 | 1/1981 |
| FR | 1.361.393 | 4/1964 |
| FR | 2.183.236 | 12/1973 |
| GB | 1 400 676 | 7/1975 |
| GB | 1 456 674 | 11/1976 |
| GB | 1 488 420 | 10/1977 |
| GB | 2 068 366 A | 8/1981 |
| GB | 1 600 457 | 10/1981 |
| JP | 49-92044 | 9/1974 |
| JP | 49-101355 | 9/1974 |
| JP | 52-100464 | 8/1977 |
| JP | 55-15445 A | 2/1980 |
| JP | 56-110697 | 9/1981 |
| WO | WO 82/00464 | 2/1982 |
| WO | WO 92/02530 | 2/1992 |
| WO | WO 94/09792 | 5/1994 |
| WO | WO 00/39139 | 7/2000 |
| WO | WO 01/54691 A1 | 8/2001 |
| WO | WO 02/053188 A1 | 7/2002 |
| WO | WO 03/059246 A2 | 7/2003 |
| WO | WO 03/101405 A2 | 12/2003 |
| WO | WO 03/105774 A2 | 12/2003 |
| WO | WO 2005/041984 A1 | 5/2005 |
| WO | WO 2006/052930 A1 | 5/2006 |
| WO | WO 2007/028012 A2 | 3/2007 |
| WO | WO 2007/064954 A2 | 6/2007 |
| WO | WO 2007/088999 A1 | 8/2007 |
| WO | WO 2008/006583 A1 | 1/2008 |
| WO | WO 2008/092690 A1 | 8/2008 |
| WO | WO 2008/124821 A1 | 10/2008 |
| WO | WO 2009/067692 A1 | 5/2009 |
| WO | WO 2010/030690 A1 | 3/2010 |
| WO | WO 2010/030704 A2 | 3/2010 |
| WO | WO 2010/042850 A1 | 4/2010 |
| WO | WO 2010/042851 A1 | 4/2010 |
| WO | WO 2010/132757 A2 | 11/2010 |
| WO | WO 2010/132759 A1 | 11/2010 |
| WO | WO 2010/132760 A1 | 11/2010 |
| WO | WO 2010/132765 A2 | 11/2010 |
| WO | WO 2010/132768 A1 | 11/2010 |
| WO | WO 2010/132770 A1 | 11/2010 |
| WO | WO 2010/132777 A2 | 11/2010 |
| WO | WO 2010/132839 A2 | 11/2010 |
| WO | WO 2010/147836 A1 | 12/2010 |
| WO | WO 2011/044498 A1 | 4/2011 |
| WO | WO 2011/044501 A2 | 4/2011 |
| WO | WO 2011/044502 A1 | 4/2011 |
| WO | WO 2011/044503 A1 | 4/2011 |
| WO | WO 2011/044538 A1 | 4/2011 |
| WO | WO 2012/067978 A1 | 5/2012 |

OTHER PUBLICATIONS

Budavari (ed.), "The Merck Index, spalte 1559, butirosin," Merck Index, *Encyclopedia of Chemicals, Drugs, and Biologicals*. 12th edition. Whitehouse Station: Merck & Co., Inc., pp. 252-253, 1996.

Cavender et al., "Trifluoromethanesulfonyl Azide. Its Reaction with Alkyl Amines to Form Alkyl Azides," *J. Org. Chem.* 37(22):3567-3569, 1972.

Chen et al., "Structure-toxicity relationship of aminoglycosides: Correlation of 2'-amine basicity with acute toxicity in pseudo-disaccharide scaffolds," *Bioorganic & Medicinal Chemistry* 16:8940-8951, 2008.

Chow et al., "A Structural Basis for RNA-Ligand Interactions," *Chem. Rev.* 97(5):1489-1513, Jul./Aug. 1997.

Ding et al., "Efficient synthesis of neomycin B related aminoglycosides," *Tetrahedron Letters* 41:4049-4052, 2000.

Dozzo et al., "New aminoglycoside antibiotics," *Expert Opin. Ther. Patents* 20(10):1-21, 2010.

François et al., "Antibacterial Aminoglycosides with a Modified Mode of Binding to the Ribosomal-RNA Decoding Site," *Angew. Chem. Int. Ed.* 43:6735-6738, 2004.

Georgiadas et al., "Synthesis of Amino Acid Derivatives of Neamine and 2-Deoxystreptamine to Be Used as Mutasynthons," *J. Carbohydrate Chemistry* 10(5):739-748, 1991.

Greenberg et al., "Design and Synthesis of New Aminoglycoside Antibiotics Containing Neamine as an Optimal Core Structure: Correlation of Antibiotic Activity with in Vitro Inhibition of Translation," *J. Am. Chem. Soc.* 121(28):6527-6541, 1999.

Greene, "Protective Groups in Organic Synthesis," John Wiley & Sons, Inc., New York, p. 29-39, 1981.

Hanessian et al., "Aminoglycoside antibiotics: Chemical conversion of neomycin B, paromomycin, and lividomycin B into bioactive pseudosaccharides," *Canadian Journal of Chemistry* 56(11):1482-1491, Jun. 1, 1978.

Hanessian et al., "Aminoglycoside Antibiotics 4'-Deoxyneomycin and 4'-Deoxyparomamine," *The Journal of Antibiotics* 33(6):675-678, Jun. 1980.

Hanessian et al., "Probing the functional requirements of the L-haba side-chain of amikacin-synthesis, 16S A-site or rRNA binding, and antibacterial activity," *Tetrahedron* 59: 995-1007, 2003.

Hanessian et al., "Probing the ribosomal RNA A-site with functionally diverse analogues of paromomycin-synthesis of ring I mimetics," *Tetrahedron* 63:827-846, 2007.

Hermansky, "Neomycin N-methanesulfonate," Database CAPLUS on STN, Accession No. 60:11121, 1962, 2 pages.

Hoshi et al., "Amikacin Analogs with a Fluorinated Amino Acid Side Chain," *The Journal of Antibiotics* 43(7):858-872, Jul. 1990.

Kane et al., "Basicity of the Amino Groups of the Aminoglycoside Amikacin Using Capillary Electrophoresis and Coupled CE-MS-MS Techniques," *Analytical Chemistry* 73(16):4028-4036, Aug. 15, 2001.

(56) References Cited

OTHER PUBLICATIONS

Kondo et al., "Crystal Structure of the Bacterial Ribosomal Decoding Site Complexed with a Synthetic Doubly Functionalized Paromomycin Derivative: a New Specific Binding Mode to an A-Minor Motif Enhances in vitro Antibacterial Activity," *ChemMedChem* 2:1631-1638, 2007.

Kumar et al., "Aminoglycoside Antibiotics. 4. Regiospecific Partial Synthesis of Ribostamycin and 4"-Thioribostamycin," *J. Org. Chem.* 46(21):4298-4300, 1981.

Lesniak et al., "An isocratic separation of underivatized gentamicin components, H NMR assignment and protonation pattern," *Carbohydrate Research* 338:2853-2862, 2003.

Li et al., "Investigation of the Regioselectivity for the Staudinger Reaction and Its Application for the Synthesis of Aminoglycosides with N-1 Modification," *J. Org. Chem.* 72(11):4055-4066, 2007.

Li et al., "Guanidine/Pd(OAc)$_2$-Catalyzed Room Temperature Suzuki Cross-Coupling Reaction in Aqueous Media under Aerobic Conditions," *J. Org. Chem.* 72(11):4067-4072, 2007.

Llewellyn et al., "Chemoenzymatic acylation of aminoglycoside antibiotics," *Chem. Commun.* 32:3786-3788, 2008.

Marrero-Ponce et al., "Non-stochastic and stochastic linear indices of the molecular pseudograph's atom-adjacency matrix: a novel approach for computational in silico screening and "rational" selection of new lead antibacterial agents," *J. Mol. Model.* 12: 255-271, 2006.

Marrero-Ponce et al., "Atom, atom-type, and total nonstochastic and stochastic quadratic fingerprints: a promising approach for modeling of antibacterial activity," *Bioorganic & Medicinal Chemistry* 13:2881-2899, 2005.

Moazed et al., "Interaction of antibiotics with functional sites in 16S ribosomal RNA," *Nature* 327:389-394, Jun. 4, 1987.

Narita et al., "Synthesis and Activity of Butirosin Derivatives with 5"-Amidino and 5"-Guanidino Substituents," *The Journal of Antibiotics* 44(1):86-92, Jan. 1991.

O'Shea et al., "Physicochemical Properties of Antibacterial Compounds: Implications for Drug Discovery," *Journal of Medicinal Chemistry* 51(10):2871-2878, May 22, 2008.

Pénasse et al., "Sur quelques dérivés mono N-alcoylés de la néomycine et de la paromomycine," *Bulletin de la Societe chimique de France* 7:2391-2394, Jul. 1969.

Scholl et al., "Synthesis and Activity of a New Generation of Ruthenium-Based Olefin Metathesis Catalysts Coordinated with 1,3-Dimesityl-4,5-dihydroimidazol-2-ylidene Ligands," *Organic Letters* 1(6):953-956, 1999.

Shier et al., "Chemistry and Biochemistry of the Neomycins. XVI Synthesis and Bioactivity of Hexa-N-Benzylneomycins," *The Journal of Antibiotics* 26(10):547-550, Oct. 1973.

Sunada et al., "Enzymatic 1-N-Acetylation of Paromomycin by an Actinomycete Strain #8 with Multiple Aminoglycoside Resistance and Paromomycin Sensitivity," *The Journal of Antibiotics* 52(9):809-814, Sep. 1999.

Takahashi et al., "Syntheses of 1-Epikanamycin A and Its 1-N-[(S)-4-Amino-2-hydroxybutyryl] Derivative," *Bull. Chem. Soc. Jpn.* 56(6):1807-1811, Jun. 1983.

Takahashi et al., "Study on fluorination-toxicity relationships. Syntheses of 1-N-[(2R,3R)- and (2R,3S)-4-amino-3-fluoro-2-hydroxybutanoyl] derivatives of kanamycins," *Carbohydrate Research* 249:57-76, 1993.

Takahashi et al., "Synthesis of 1-N-[(2S,4S)- and (2S,4R)-5-amino-4-fluoro-2-hydroxypentanoyl]dibekacins (study on structure-toxicity relationships)," *Carbohydrate Research* 306:349-360, 1998.

Takamoto et al., "Aminoglycoside Antibiotics: Chemical Transformation of Paromomycin Into a Bioactive Pseudotrisaccharide," *Tetrahedron Letters* 46:4009-4012, 1974.

Takeda et al., "Mutational Biosynthesis of Butirosin Analogs II. 3',4'-Dideoxy-6'-N-Methylbutirosins, New Semisynthetic Aminoglycosides," *The Journal of Antibiotics* 31(10):1031-1038, Oct. 1978.

Takeda et al., "Mutational Biosynthesis of Butirosin Analogs III. 6'-N-Methylbutirosins and 3',4'-Dideoxy-6'-C-Methylbutirosins, New Semisynthetic Aminoglycosides," *The Journal of Antibiotics* 31(10):1039-1045, Oct. 1978.

Tamura et al., "The Synthesis of Destomycin C, a Typical Pseudo-Trisaccharide of Destomycin-Group Antibiotics," *Carbohydrate Research* 174:181-199, 1988.

Taniyama et al., "Antibiotics Aminosidin. II. Some Amino Derivatives of Aminosidin and Their Biological Activity," *Chem. Pharm. Bull.* 21(3):609-615, Mar. 1973.

Tok et al., "Binding of Aminoglycoside Antibiotics with Modified A-site 16S rRNA Construct Containing Non-Nucleotide Linkers," *Bioorganic & Medicinal Chemistry Letters* 12:365-370, 2002.

Torn et al., "Synthesis of 5"-Deoxy-5"-Fluorolividomycin B," *Bull. Chem. Soc. Jpn*, 56:5, 1522-1526, 1983.

Umezawa et al., "Synthesis and Antibacterial Activity of 6'-N-Alkyl Derivatives of 1-N-[(S)-4-Amino-2-Hydroxybutyryl]-Kanamycin," *The Journal of Antibiotics* 28(6):483-485, Jun. 1975.

Van Straten et al., "An Expeditious Route to the Synthesis of Adenophostin A," *Tetrahedron* 53(18):6509-6522, 1997.

Wallis et al., "The Binding of Antibiotics to RNA," *Prog. Biophys. molec. Biol.* 67(2/3):141-154, 1997.

Watanabe et al., "Syntheses of 6'-Amino-6'-Deoxylividomycin B and 6'-Deoxy-6'-Methylamino- and 6'-Deoxy-6'-(2-Hydroxyethylamino)-Lividomycin B," *The Journal of Antibiotics* 26(12):802-804, Dec. 1973.

Watanabe et al., "Synthesis of 6'-Amino-1-N-[(S)-4-Amino-2-Hydroxybutyryl]-6'-Deoxylividomycin A," *Bulletin of the Chemical Society of Japan* 48(8):2303-2305, Aug. 1975.

Watanabe et al., "Synthesis of 1-N-[(S)-4-Amino-2-hydroxybutyryl]lividomycin A," *Bulletin of the Chemical Society of Japan* 48(7):2124-2126, Jul. 1975.

Watanabe et al., "Synthesis of 1-N-((s)-4-Amino-2-Hydroxybutyryl) Lividomycin A," *The Journal of Antibiotics* 26(5):310-312, May 1973.

Wolff, Manfred E., "Burger's Medicinal Chemistry and Drug Discovery, Fifth Edition, vol. 1: Principles and Practice," John Wiley & Sons, Inc., 1995, pp. 975-977.

Yamasaki et al., "Synthesis and Biological Activity of 1-N-[4-(Substituted)Amidino and Guanidino-2-Hydroxybutyryl]Kanamycins A and B," *The Journal of Antibiotics* 44(6):646-658, Jun. 1991.

Zaloom et al., "Preparation of Azido Derivatives from Amino Acids and Peptides by Diazo Transfer," *J. Org. Chem* 46(25):5173-5176, 1981.

International Search Report for PCT International Application No. PCT/US2005/040364, mailed Mar. 29, 2006, (4 pages).

International Search Report for PCT International Application No. PCT/US2006/034216, mailed May 3, 2007, (5 pages).

International Search Report for PCT International Application No. PCT/US2006/046122, mailed Jun. 21, 2007, (7 pages).

International Search Report for PCT International Application No. PCT/US2008/059904, mailed Jun. 19, 2008, (4 pages).

International Search Report for PCT International Application No. PCT/US2009/056391, mailed Feb. 15, 2010, (7 pages).

International Search Report for PCT International Application No. PCT/US2009/056407, mailed Mar. 30, 2010, (4 pages).

International Search Report for PCT International Application No. PCT/US2009/060211, mailed Dec. 29, 2009, (3 pages).

International Search Report for PCT International Application No. PCT/US2009/060212, mailed Dec. 9, 2009, (2 pages).

International Search Report for PCT International Application No. PCT/US2010/052045, mailed Feb. 17, 2011, (4 pages).

International Search Report for PCT International Application No. PCT/US2010/052109, mailed Feb. 23, 2011, (4 pages).

International Search Report for PCT International Application No. PCT/US2010/052040, mailed Feb. 23, 2011, (3 pages).

International Search Report for PCT International Application No. PCT/US2010/052044, mailed Feb. 23, 2011, (4 pages).

International Search Report for PCT International Application No. PCT/US2010/052043, mailed May 2, 2011, (5 pages).

International Search Report for PCT International Application No. PCT/US2011/060513, mailed Mar. 27, 2011, (4 pages).

(56) References Cited

OTHER PUBLICATIONS

Invitation to Pay Additional Fees for PCT International Application No. PCT/US2010/052043, mailed Feb. 24, 2011, (8 pages).
International Preliminary Report on Patentability for PCT/US2005/040364, mailed May 8, 2007, (9 pages).
International Preliminary Report on Patentability for PCT/US2006/034216, mailed Mar. 4, 2008, (8 pages).
International Preliminary Report on Patentability for PCT/US2009/056391, mailed Mar. 15, 2011, (9 pages).
International Preliminary Report on Patentability for PCT/US2006/046122, mailed Jun. 4, 2008, (11 pages).
International Preliminary Report on Patentability for PCT/US2008/059904, mailed Oct. 13, 2009, (7 pages).
International Preliminary Report on Patentability for PCT/US2009/056407, mailed Mar. 15, 2011, (5 pages).
International Preliminary Report on Patentability for PCT/US2009/060212, mailed Apr. 12, 2011, (6 pages).
International Preliminary Report on Patentability for PCT/US2009/060211, mailed Apr. 12, 2011, (7 pages).
International Preliminary Report on Patentability for PCT/US2010/052040, mailed Apr. 19, 2012, (7 pages).
International Preliminary Report on Patentability for PCT/US2010/052043, mailed Apr. 19, 2012, (12 pages).
International Preliminary Report on Patentability for PCT/US2010/052045, mailed Apr. 19, 2012, (7 pages).
International Preliminary Report on Patentability for PCT/US2010/052044, mailed Apr. 19, 2012, (8 pages).
Written Opinion for PCT/US2005/040364, mailed Mar. 29, 2006, (8 pages).
Written Opinion for PCT/US2006/034216, mailed May 3, 2007, (7 pages).
Written Opinion for PCT/US2006/046122, mailed Jun. 21, 2007, (10 pages).
Written Opinion for PCT/US2008/059904, mailed Jun. 19, 2008, (7 pages).
Written Opinion for PCT/US2009/056391, mailed Feb. 15, 2010, (8 pages).
Written Opinion for PCT/US2009/056407, mailed Mar. 30, 2010, (4 pages).
Written Opinion for PCT/US2009/060211, mailed Dec. 29, 2009, (6 pages).
Written Opinion for PCT/US2009/060212, mailed Dec. 9, 2009, (5 pages).
Written Opinion for PCT/US2010/052045, mailed Feb. 17, 2011, (5 pages).
Written Opinion for PCT/US2010/052109, mailed Feb. 23, 2011, (6 pages).
Written Opinion for PCT/US2010/052040, mailed Feb. 23, 2011, (5 pages).
Written Opinion for PCT/US2010/052043, mailed May 2, 2011, (10 pages).
Written Opinion for PCT/US2010/052044, mailed Feb. 23, 2011, (8 pages).
Written Opinion for PCT/US2011/060513, mailed Mar. 27, 2011, (7 pages).
Non-Final Office Action for U.S. Appl. No. 12/040,615, mailed Jan. 27, 2009, (6 pages).
Non-Final Office Action for U.S. Appl. No. 12/040,615, mailed Jun. 25, 2009, (16 pages).
Notice of Abandonment for U.S. Appl. No. 12/040,615, mailed Feb. 3, 2010, (3 pages).
Non-Final Office Action for U.S. Appl. No. 13/044,226, mailed May 15, 2012, (5 pages).
Notice of Allowance for U.S. Appl. No. 13/044,226, mailed Oct. 18, 2012 (6 pages).
Non-Final Office Action for U.S. Appl. No. 09/452,606, mailed Jul. 13, 2001, (13 pages).
Office Communication for U.S. Appl. No. 09/452,606, mailed Dec. 21, 2001, (4 pages).
Final Office Action for U.S. Appl. No. 09/452,606, mailed May 7, 2002, (7 pages).
Office Communication for U.S. Appl. No. 09/452,606, mailed Feb. 5, 2003, (3 pages).
Advisory Action for U.S. Appl. No. 09/452,606, mailed Aug. 5, 2002, (3 pages).
Notice of Allowance and Fee(s) Due for U.S. Appl. No. 09/452,606, mailed Oct. 21, 2002, 3 pages.
Issue Notification for U.S. Appl. No. 09/452,606, mailed Mar. 12, 2003, 1 page.
Non-Final Office Action for U.S. Appl. No. 09/727,315, mailed Sep. 23, 2002, (7 pages).
Non-Final Office Action for U.S. Appl. No. 09/727,315, mailed Jan. 14, 2003, (10 pages).
Final Office Action for U.S. Appl. No. 09/727,315, mailed Apr. 28, 2003, (7 pages).
Notice of Allowance and Fee(s) Due for U.S. Appl. No. 09/727,315, mailed Aug. 25, 2003, (7 pages).
Notice of Allowance and Fee(s) Due for U.S. Appl. No. 09/727,315, mailed Jan. 28, 2004, (3 pages).
Issue Notification for U.S. Appl. No. 09/727,315, mailed Jun. 17, 2004, (1 page).
Non-Final Office Action for U.S. Appl. No. 10/299,220, mailed Nov. 3, 2003, (11 pages).
Notice of Non-Compliant Amendment (37 CFR 1.121) for U.S. Appl. No. 10/299,220, mailed Feb. 10, 2004, (2 pages).
Final Office Action for U.S. Appl. No. 10/299,220, mailed May 13, 2004, (10 pages including Appendices A-C).
Advisory Action for U.S. Appl. No. 10/299,220, mailed Aug. 6, 2004, (3 pages).
Notice of Allowance and Fee(s) Due for U.S. Appl. No. 10/299,220, mailed Oct. 13, 2004, (5 pages).
Response to Rule 312 Communication for U.S. Appl. No. 10/299,220, mailed Oct. 13, 2005, (2 pages).
Issue Notification for U.S. Appl. No. 10/299,220, mailed Nov. 2, 2005, (1 page).
Non-Final Office Action for U.S. Appl. No. 12/130,048, mailed May 27, 2010, (9 pages).
Notice of Allowance and Fee(s) Due for U.S. Appl. No. 12/130,048, mailed Dec. 14, 2010, (4 pages).
Issue Notification for U.S. Appl. No. 12/130,048, mailed Feb. 2, 2011, (1 page).
Non-Final Office Action for U.S. Appl. No. 12/100,981, mailed Nov. 27, 2009, (10 pages).
Non-Final Office Action for U.S. Appl. No. 12/100,981, mailed Feb. 26, 2010, (7 pages).
Final Office Action for U.S. Appl. No. 12/100,981, mailed Oct. 4, 2010, (8 pages).
Non-Final Office Action for U.S. Appl. No. 12/100,981, mailed Nov. 29, 2011, (7 pages).
Final Office Action for U.S. Appl. No. 12/100,981, mailed Jul. 6, 2012, (8 pages).
Non-Final Office Action for U.S. Appl. No. 12/100,981, mailed Feb. 20, 2013, (7 pages).
Non-Final Office Action for U.S. Appl. No. 13/044,234, mailed Apr. 27, 2012, (8 pages).
Notice of Allowance for U.S. Appl. No. 13/044,234, mailed Nov. 13, 2012 (5 pages).
Notice of Allowance and Fee(s) Due for U.S. Appl. No. 13/082,141, mailed Aug. 6, 2012 (9 pages).
Office Communication enclosing corrected Notice of Allowability for U.S. Appl. No. 13/082,141, mailed Sep. 5, 2012 (3 pages).
Notice of Allowance and Fee(s) Due for U.S. Appl. No. 13/082,141, mailed Oct. 9, 2012 (5 pages).
Notice of Allowance and Fee(s) Due for U.S. Appl. No. 13/082,143, mailed Aug. 9, 2012 (9 pages).
Notice of Allowance and Fee(s) Due for U.S. Appl. No. 13/082,143, mailed Oct. 9, 2012 (4 pages).
Non-Final Office Action for U.S. Appl. No. 13/441,696, mailed Sep. 13, 2012 (10 pages).
Notice of Allowance and Fee(s) Due for U.S. Appl. No. 13/441,696, mailed Feb. 21, 2013, (7 pages).

(56) References Cited

OTHER PUBLICATIONS

Notice of Allowance and Fee(s) Due for U.S. Appl. No. 13/295,219, mailed Jul. 30, 2012 (8 pages).
(2nd) Notice of Allowance and Fee(s) Due for U.S. Appl. No. 13/295,219, mailed Oct. 3, 2012 (8 pages).
Non-Final Office Action for U.S. Appl. No. 13/344,247, mailed Feb. 27, 2013, (5 pages).
International Preliminary Report on Patentability for PCT/US2010/052109, mailed Apr. 9, 2013 (8 pages).
International Preliminary Report on Patentability for PCT/US2011/060513, mailed May 21, 2013 (7 pages).
Non-Final Office Action for U.S. Appl. No. 13/441,693, mailed May 6, 2013 (8 pages).
Non-Final Office Action for U.S. Appl. No. 13/441,699, mailed May 7, 2013 (10 pages).
Non-Final Office Action for U.S. Appl. No. 13/441,701, mailed May 9, 2013 (10 pages).
Notice of Allowance for U.S. Appl. No. 13/344,247, mailed Jun. 17, 2013 (8 pages).
Response to Rule 312 Communication for U.S. Appl. No. 13/344,247, mailed Aug. 9, 2013 (2 pages).

* cited by examiner

ANTIBACTERIAL AMINOGLYCOSIDE ANALOGS

CROSS-REFERENCE TO RELATED APPLICATIONS

This application is a continuation of U.S. patent application Ser. No. 13/295,219, filed Nov. 14, 2011, now U.S. Pat. No. 8,318,685, which claims the benefit under 35 U.S.C. §119(e) of U.S. Provisional Patent Application No. 61/414,762, filed Nov. 17, 2010, and U.S. Provisional Patent Application No. 61/505,371, filed Jul. 7, 2011. The foregoing applications are incorporated herein by reference in their entireties.

STATEMENT OF GOVERNMENT INTEREST

This invention was made with government support under Contract No. HHSN272200800043C, awarded by the National Institutes of Health. The government has certain rights in this invention.

BACKGROUND

1. Field

The present invention is directed to novel aminoglycoside compounds, and methods for their preparation and use as therapeutic or prophylactic agents.

2. Description of the Related Art

A particular interest in modern drug discovery is the development of novel low molecular weight drugs that work by binding to RNA. RNA, which serves as a messenger between DNA and proteins, was thought to be an entirely flexible molecule without significant structural complexity. Recent studies have revealed a surprising intricacy in RNA structure. RNA has a structural complexity rivaling proteins, rather than simple motifs like DNA. Genome sequencing reveals both the sequences of the proteins and the mRNAs that encode them. Since proteins are synthesized using an RNA template, such proteins can be inhibited by preventing their production in the first place by interfering with the translation of the mRNA. Since both proteins and the RNAs are potential drug targeting sites, the number of targets revealed from genome sequencing efforts is effectively doubled. These observations unlock a new world of opportunities for the pharmaceutical industry to target RNA with small molecules.

Classical drug discovery has focused on proteins as targets for intervention. Proteins can be extremely difficult to isolate and purify in the appropriate form for use in assays for drug screening. Many proteins require post-translational modifications that occur only in specific cell types under specific conditions. Proteins fold into globular domains with hydrophobic cores and hydrophilic and charged groups on the surface. Multiple subunits frequently form complexes, which may be required for a valid drug screen. Membrane proteins usually need to be embedded in a membrane to retain their proper shape. The smallest practical unit of a protein that can be used in drug screening is a globular domain. The notion of removing a single alpha helix or turn of a beta sheet and using it in a drug screen is not practical, since only the intact protein may have the appropriate 3-dimensional shape for drug binding. Preparation of biologically active proteins for screening is a major limitation in classical high throughput screening. Quite often the limiting reagent in high throughput screening efforts is a biologically active form of a protein which can also be quite expensive.

For screening to discover compounds that bind RNA targets, the classic approaches used for proteins can be superceded with new approaches. All RNAs are essentially equivalent in their solubility, ease of synthesis or use in assays. The physical properties of RNAs are independent of the protein they encode. They may be readily prepared in large quantity through either chemical or enzymatic synthesis and are not extensively modified in vivo. With RNA, the smallest practical unit for drug binding is the functional subdomain. A functional subdomain in RNA is a fragment that, when removed from the larger RNA and studied in isolation, retains its biologically relevant shape and protein or RNA-binding properties. The size and composition of RNA functional subdomains make them accessible by enzymatic or chemical synthesis. The structural biology community has developed significant experience in identification of functional RNA subdomains in order to facilitate structural studies by techniques such as NMR spectroscopy. For example, small analogs of the decoding region of 16S rRNA (the A-site) have been identified as containing only the essential region, and have been shown to bind antibiotics in the same fashion as the intact ribosome.

The binding sites on RNA are hydrophilic and relatively open as compared to proteins. The potential for small molecule recognition based on shape is enhanced by the deformability of RNA. The binding of molecules to specific RNA targets can be determined by global conformation and the distribution of charged, aromatic, and hydrogen bonding groups off of a relatively rigid scaffold. Properly placed positive charges are believed to be important, since long-range electrostatic interactions can be used to steer molecules into a binding pocket with the proper orientation. In structures where nucleobases are exposed, stacking interactions with aromatic functional groups may contribute to the binding interaction. The major groove of RNA provides many sites for specific hydrogen bonding with a ligand. These include the aromatic N7 nitrogen atoms of adenosine and guanosine, the O4 and O6 oxygen atoms of uridine and guanosine, and the amines of adenosine and cytidine. The rich structural and sequence diversity of RNA suggests to us that ligands can be created with high affinity and specificity for their target.

Although our understanding of RNA structure and folding, as well as the modes in which RNA is recognized by other ligands, is far from being comprehensive, significant progress has been made in the last decade (see, e.g., Chow, C. S.; Bogdan, F. M., Chem. Rev., 1997, 97, 1489 and Wallis, M. G.; Schroeder, R., Prog. Biophys. Molec. Biol. 1997, 67, 141). Despite the central role RNA plays in the replication of bacteria, drugs that target these pivotal RNA sites of these pathogens are scarce. The increasing problem of bacterial resistance to antibiotics makes the search for novel RNA binders of crucial importance.

Certain small molecules can bind and block essential functions of RNA. Examples of such molecules include the aminoglycoside antibiotics and drugs such as erythromycin which binds to bacterial rRNA and releases peptidyl-tRNA and mRNA. Aminoglycoside antibiotics have long been known to bind RNA. They exert their antibacterial effects by binding to specific target sites in the bacterial ribosome. For the structurally related antibiotics neamine, ribostamycin, neomycin B, and paromomycin, the binding site has been localized to the A-site of the prokaryotic 16S ribosomal decoding region RNA (see Moazed, D.; Noller, H. F., Nature, 1987, 327, 389). Binding of aminoglycosides to this RNA target interferes with the fidelity of mRNA translation and results in miscoding and truncation, leading ultimately to bacterial cell death (see Alper, P. B.; Hendrix, M.; Sears, P.; Wong, C., *J. Am. Chem. Soc.*, 1998, 120, 1965).

There is a need in the art for new chemical entities that work against bacteria with broad-spectrum activity. Perhaps the biggest challenge in discovering RNA-binding antibacterial drugs is identifying vital structures common to bacteria that can be disabled by small molecule drug binding. A challenge in targeting RNA with small molecules is to develop a chemical strategy which recognizes specific shapes of RNA. There are three sets of data that provide hints on how to do this: natural protein interactions with RNA, natural product antibiotics that bind RNA, and man-made RNAs (aptamers) that bind proteins and other molecules. Each data set, however, provides different insights to the problem.

Several classes of drugs obtained from natural sources have been shown to work by binding to RNA or RNA/protein complexes. These include three different structural classes of antibiotics: thiostreptone, the aminoglycoside family and the macrolide family of antibiotics. These examples provide powerful clues to how small molecules and targets might be selected. Nature has selected RNA targets in the ribosome, one of the most ancient and conserved targets in bacteria. Since antibacterial drugs are desired to be potent and have broad-spectrum activity, these ancient processes, fundamental to all bacterial life, represent attractive targets. The closer we get to ancient conserved functions the more likely we are to find broadly conserved RNA shapes. It is important to also consider the shape of the equivalent structure in humans, since bacteria were unlikely to have considered the therapeutic index of their RNAs while evolving them.

A large number of natural antibiotics exist, these include the aminoglycosides, such as, kirromycin, neomycin, paromomycin, thiostrepton, and many others. They are very potent, bactericidal compounds that bind RNA of the small ribosomal subunit. The bactericidal action is mediated by binding to the bacterial RNA in a fashion that leads to misreading of the genetic code. Misreading of the code during translation of integral membrane proteins is thought to produce abnormal proteins that compromise the barrier properties of the bacterial membrane.

Antibiotics are chemical substances produced by various species of microorganisms (bacteria, fungi, actinomycetes) that suppress the growth of other microorganisms and may eventually destroy them. However, common usage often extends the term antibiotics to include synthetic antibacterial agents, such as the sulfonamides, and quinolines, that are not products of microbes. The number of antibiotics that have been identified now extends into the hundreds, and many of these have been developed to the stage where they are of value in the therapy of infectious diseases. Antibiotics differ markedly in physical, chemical, and pharmacological properties, antibacterial spectra, and mechanisms of action. In recent years, knowledge of molecular mechanisms of bacterial, fungal, and viral replication has greatly facilitated rational development of compounds that can interfere with the life cycles of these microorganisms.

At least 30% of all hospitalized patients now receive one or more courses of therapy with antibiotics, and millions of potentially fatal infections have been cured. At the same time, these pharmaceutical agents have become among the most misused of those available to the practicing physician. One result of widespread use of antimicrobial agents has been the emergence of antibiotic-resistant pathogens, which in turn has created an ever-increasing need for new drugs. Many of these agents have also contributed significantly to the rising costs of medical care.

When the antimicrobial activity of a new agent is first tested, a pattern of sensitivity and resistance is usually defined. Unfortunately, this spectrum of activity can subsequently change to a remarkable degree, because microorganisms have evolved the array of ingenious alterations discussed above that allow them to survive in the presence of antibiotics. The mechanism of drug resistance varies from microorganism to microorganism and from drug to drug.

The development of resistance to antibiotics usually involves a stable genetic change, inheritable from generation to generation. Any of the mechanisms that result in alteration of bacterial genetic composition can operate. While mutation is frequently the cause, resistance to antimicrobial agents may be acquired through transfer of genetic material from one bacterium to another by transduction, transformation or conjugation.

For the foregoing reasons, while progress has been made in this field, there is a need for new chemical entities that possess antibacterial activity. Further, in order to accelerate the drug discovery process, new methods for synthesizing aminoglycoside antibiotics are needed to provide an array of compounds that are potentially new drugs for the treatment of bacterial infections. The present invention fulfills these needs and provides further related advantages.

BRIEF SUMMARY

In brief, the present invention is directed to novel aminoglycoside compounds, having antibacterial activity, including stereoisomers, prodrugs and pharmaceutically acceptable salts thereof, and the use of such compounds in the treatment of bacterial infections.

In one embodiment, compounds having the following structure (I) are provided:

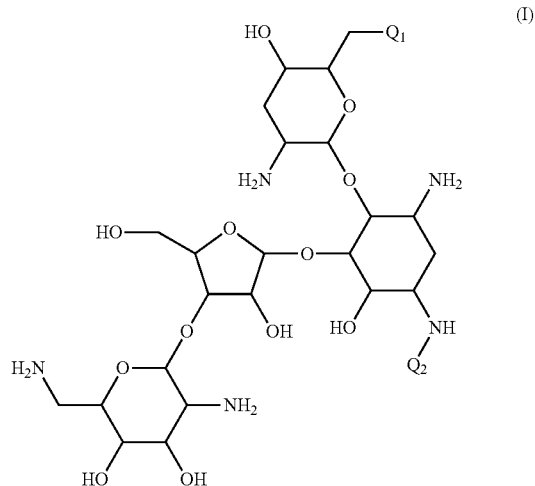

or a stereoisomer, prodrug or pharmaceutically acceptable salt thereof, wherein:

$Q_1$ is —$NHR_1$;

$Q_2$ is

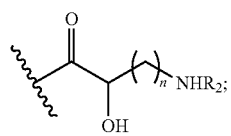

$R_1$ is $C_2$-$C_6$ alkyl substituted with at least one hydroxyl;

$R_2$ is hydrogen or $C_1$-$C_6$ alkyl optionally substituted with one or more halogen, hydroxyl or amino; and n is an integer from 1 to 4.

In another embodiment, a pharmaceutical composition is provided comprising a compound having structure (I), or a stereoisomer, prodrug or pharmaceutically acceptable salt thereof, and a pharmaceutically acceptable carrier, diluent or excipient.

In another embodiment, a method of using a compound having structure (I) in therapy is provided. In particular, the present invention provides a method of treating a bacterial infection in a mammal comprising administering to a mammal in need thereof an effective amount of a compound having structure (I), or a stereoisomer, prodrug or pharmaceutically acceptable salt thereof. In addition, the present invention provides a method of treating a bacterial infection in a mammal comprising administering to a mammal in need thereof an effective amount of a pharmaceutical composition comprising a compound having structure (I), or a stereoisomer, prodrug or pharmaceutically acceptable salt thereof, and a pharmaceutically acceptable carrier, diluent or excipient. In a more specific embodiment of the foregoing, the bacterial infection is caused by an *Acinetobacter baumannii* bacterium. In another more specific embodiment of the foregoing, the bacterial infection is caused by a *Pseudomonas aeruginosa* bacterium.

These and other aspects of the invention will be apparent upon reference to the following detailed description.

DETAILED DESCRIPTION

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the —$NH_2$ radical.

"Hydroxy" or "hydroxyl" refers to the —OH radical.

"Alkyl" refers to a straight or branched hydrocarbon chain radical consisting solely of carbon and hydrogen atoms, which is saturated or unsaturated (i.e., contains one or more double and/or triple bonds), having from one to twelve carbon atoms ($C_1$-$C_{12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group may be optionally substituted.

"Halo" or "halogen" refers to bromo, chloro, fluoro or iodo.

The term "substituted" used herein means an alkyl group wherein at least one hydrogen atom is replaced by a bond to a non-hydrogen atom such as, but not limited to: a halogen atom such as F, Cl, Br, and I; an oxygen atom in a hydroxyl group; and a nitrogen atom in an amino group.

The term "protecting group," as used herein, refers to a labile chemical moiety which is known in the art to protect reactive groups including without limitation, hydroxyl and amino groups, against undesired reactions during synthetic procedures. Hydroxyl and amino groups which protected with a protecting group are referred to herein as "protected hydroxyl groups" and "protected amino groups", respectively. Protecting groups are typically used selectively and/or orthogonally to protect sites during reactions at other reactive sites and can then be removed to leave the unprotected group as is or available for further reactions. Protecting groups as known in the art are described generally in Greene and Wuts, Protective Groups in Organic Synthesis, 3rd edition, John Wiley & Sons, New York (1999). Groups can be selectively incorporated into aminoglycosides of the invention as precursors. For example an amino group can be placed into a compound of the invention as an azido group that can be chemically converted to the amino group at a desired point in the synthesis. Generally, groups are protected or present as a precursor that will be inert to reactions that modify other areas of the parent molecule for conversion into their final groups at an appropriate time. Further representative protecting or precursor groups are discussed in Agrawal, et al., Protocols for Oligonucleotide Conjugates, Eds, Humana Press; New Jersey, 1994; Vol. 26 pp. 1-72. Examples of "hydroxyl protecting groups" include, but are not limited to, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p-nitrobenzyl, triphenylmethyl, trimethylsilyl, triethylsilyl, t-butyldimethylsilyl, t-butyldiphenylsilyl (TBDPS), triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate. Examples of "amino protecting groups" include, but are not limited to, carbamate-protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide protecting groups, such as formyl, acetyl, trihaloacetyl, benzoyl, and nitrophenylacetyl; sulfonamide-protecting groups, such as 2-nitrobenzenesulfonyl; and imine and cyclic imide protecting groups, such as phthalimido and dithiasuccinoyl.

"Prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxyl or amino group is bonded to any group that, when the prodrug of the compound of the invention is administered to a mammalian subject, cleaves to form a free hydroxyl or free amino group, respectively. Examples of prodrugs include, but are not limited to, acetate, formate and benzoate derivatives of alcohol or amide derivatives of amine functional groups in the compounds of the invention and the like.

The invention disclosed herein is also meant to encompass all pharmaceutically acceptable compounds of structure (I) being isotopically-labelled by having one or more atoms replaced by an atom having a different atomic mass or mass number. Examples of isotopes that can be incorporated into the disclosed compounds include isotopes of hydrogen, carbon, nitrogen, oxygen, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabelled compounds could be useful to help determine or measure the effectiveness of the compounds, by characterizing, for example, the site or mode of action, or binding affinity to pharmacologically important site of action. Certain isotopically-labelled compounds of structure (I), for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of structure (I) can generally be prepared by conventional techniques known to those skilled in the art or by processes analogous to those described in the Examples as set out below using an appropriate isotopically-labeled reagent in place of the non-labeled reagent previously employed.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted alkyl" means that the alkyl radical may or may not be substituted and that the description includes both substituted alkyl radicals and alkyl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Effective amount" or "therapeutically effective amount" refers to that amount of a compound of the invention which, when administered to a mammal, preferably a human, is sufficient to effect treatment, as defined below, of a bacterial infection in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

As noted above, in one embodiment of the present invention, compounds having antibacterial activity are provided, the compounds having the following structure (I):

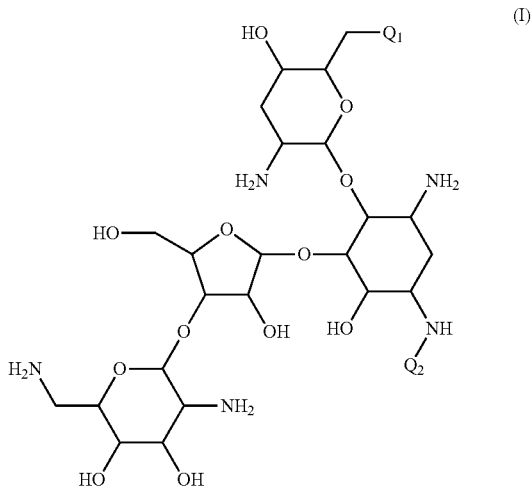

or a stereoisomer, prodrug or pharmaceutically acceptable salt thereof, wherein:

$Q_1$ is —$NHR_1$;

$Q_2$ is

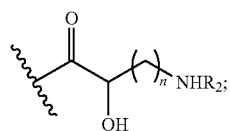

$R_1$ is $C_2$-$C_6$ alkyl substituted with at least one hydroxyl;

$R_2$ is hydrogen or $C_1$-$C_6$ alkyl optionally substituted with one or more halogen, hydroxyl or amino; and n is an integer from 1 to 4.

In further embodiments, $R_1$ is $C_2$-$C_6$ alkyl substituted with one hydroxyl. In more specific embodiments, $R_1$ is —$(CH_2)_m$OH, wherein m is an integer from 2 to 6. For example, in certain embodiments, $R_1$ is —$(CH_2)_2$OH or —$(CH_2)_3$OH. In other more specific embodiments, $R_1$ is —$(CH_2)_p$CH($CH_3$)OH, wherein p is an integer from 1 to 4. For example, in certain embodiments, $R_1$ is —$CH_2CH(CH_3)OH$ or —$(CH_2)_2CH(CH_3)OH$.

In other further embodiments, $R_1$ is $C_2$-$C_6$ alkyl substituted with two hydroxyl groups. In more specific embodiments, $R_1$ is —$CH_2CH(OH)(CH_2)_qOH$ wherein q is an integer from 1 to 4. For example, in certain embodiments, $R_1$ is —$CH_2CH(OH)CH_2OH$ or —$CH_2CH(OH)(CH_2)_2OH$. In other more specific embodiments, $R_1$ is —$(CH_2)_rCH(CH_2OH)_2$ wherein r is 0 or an integer from 1 to 3. For example, in certain embodiments, $R_1$ is —$CH_2CH(CH_2OH)_2$ or —$CH(CH_2OH)_2$.

In other further embodiments, $R_2$ is hydrogen.

In other further embodiments, $Q_2$ is:

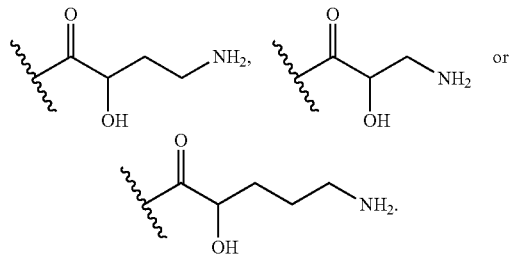

In other further embodiments, the compound has the following configuration:

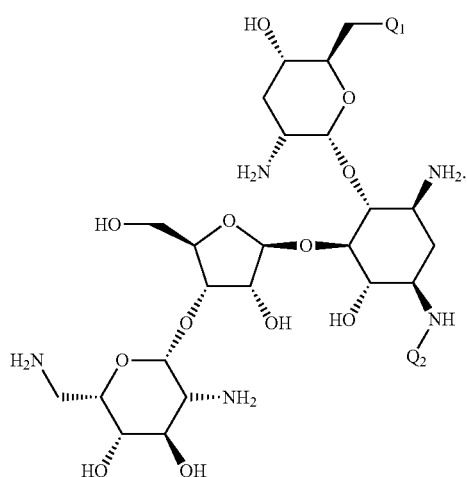

In certain embodiments, the compound is:

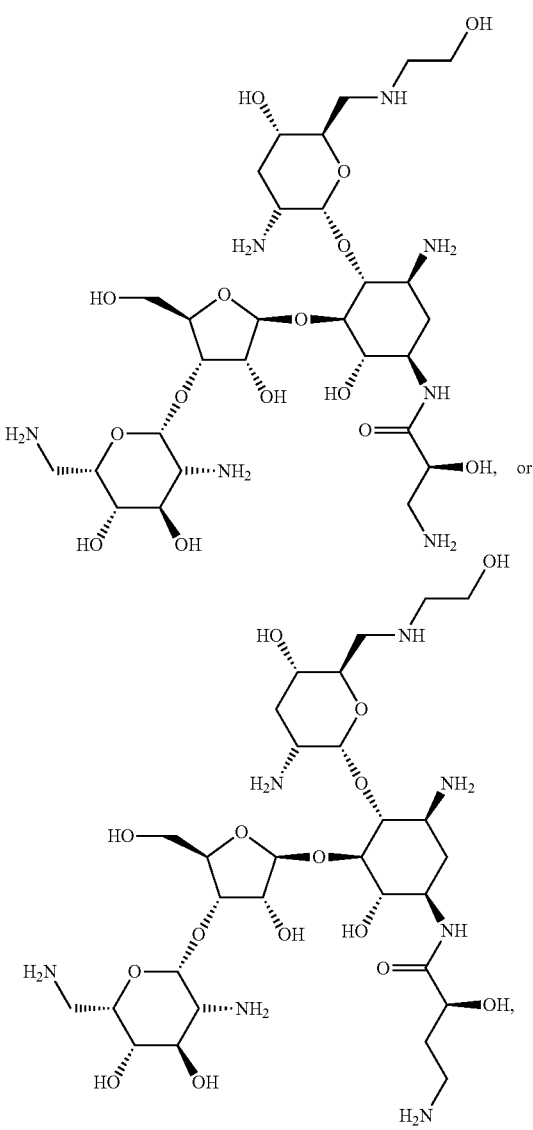

or a pharmaceutically acceptable salt thereof.

It is understood that any embodiment of the compounds of structure (I), as set forth above, and any specific substituent set forth herein for a $Q_1$, $Q_2$, $R_1$, $R_2$, n, m, p, q or r group in the compounds of structure (I), as set forth above, may be independently combined with other embodiments and/or substituents of compounds of structure (I) to form embodiments of the inventions not specifically set forth above. In addition, in the event that a list of substitutents is listed for any particular $Q_1$, $Q_2$, $R_1$, $R_2$, n, m, p, q or r group in a particular embodiment and/or claim, it is understood that each individual substituent may be deleted from the particular embodiment and/or claim and that the remaining list of substituents will be considered to be within the scope of the invention.

For the purposes of administration, the compounds of the present invention may be administered as a raw chemical or may be formulated as pharmaceutical compositions. Pharmaceutical compositions of the present invention comprise a compound of structure (I), or a stereoisomer, prodrug or pharmaceutically acceptable salt thereof, and a pharmaceutically acceptable carrier, diluent or excipient. The compound of structure (I) is present in the composition in an amount which is effective to treat a particular disease or condition of interest—that is, in an amount sufficient to treat a bacterial infection, and generally with acceptable toxicity to the patient. The antibacterial activity of compounds of structure (I) can be determined by one skilled in the art, for example, as described in the Examples below. Appropriate concentrations and dosages can be readily determined by one skilled in the art.

Compounds of the present invention possess antibacterial activity against a wide spectrum of gram positive and gram negative bacteria, as well as enterobacteria and anaerobes. Representative susceptible organisms generally include those gram positive and gram negative, aerobic and anaerobic organisms whose growth can be inhibited by the compounds of the invention such as *Staphylococcus, Lactobacillus, Streptococcus, Sarcina, Escherichia, Enterobacter, Klebsiella, Pseudomonas, Acinetobacter, Mycobacterium, Proteus, Campylobacter, Citrobacter, Nisseria, Baccillus, Bacteroides, Peptococcus, Clostridium, Salmonella, Shigella, Serratia, Haemophilus, Brucella, Francisella, Anthracis, Yersinia, Corynebacterium, Moraxella, Enterococcus*, and other organisms.

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrastemal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *Remington: The Science and Practice of Pharmacy*, 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, pharmaceutical compositions of the present invention typically are either solid or liquid form, where semi-solid, semi-liquid, suspension and gel forms are included within the forms considered herein as either solid or liquid.

As a solid composition for oral administration, the pharmaceutical compositions may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

Pharmaceutical compositions of the invention may be in the form of a liquid, for example, an elixir, syrup, solution, emulsion or suspension. The liquid may be for oral administration or for delivery by injection, as two examples. When intended for oral administration, pharmaceutical compositions of the invention typically contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

Liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. Parenteral preparations can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained.

Pharmaceutical compositions of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

Pharmaceutical compositions of the invention may be intended for rectal administration, in the form, for example, of a suppository, which will melt in the rectum and release the drug. Compositions for rectal administration may contain an oleaginous base as a suitable nonirritating excipient. Such bases include, without limitation, lanolin, cocoa butter and polyethylene glycol.

Pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

Pharmaceutical compositions of the invention in solid or liquid form may include an agent that binds to the compound of the invention and thereby assists in the delivery of the compound. Suitable agents that may act in this capacity include a monoclonal or polyclonal antibody, a protein or a liposome.

Pharmaceutical compositions of the invention may be prepared in dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

Compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

Compounds of the invention, or pharmaceutically acceptable derivatives thereof, may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

It is understood that in the present description, combinations of substituents and/or variables of the depicted formulae are permissible only if such contributions result in stable compounds.

It will also be appreciated by those skilled in the art that in the synthetic processes described herein the functional groups of intermediate compounds may need to be protected by suitable protecting groups. Such functional groups include hydroxy, amino, mercapto and carboxylic acid. As described above, suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like, and suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although a protected derivative of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

Furthermore, compounds of the invention which exist in free base or acid form can be converted to their pharmaceutically acceptable salts by treatment with the appropriate inorganic or organic base or acid by methods known to one skilled in the art. Salts of the compounds of the invention can be converted to their free base or acid form by standard techniques.

The following Examples illustrate various methods of making compounds of structure (I):

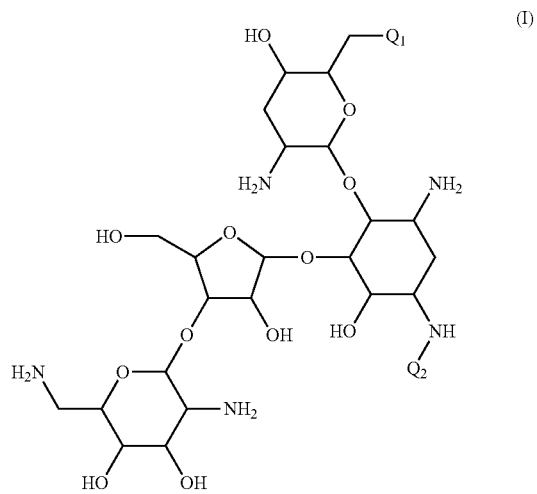

wherein $Q_1$ and $Q_2$ are as defined above. It is understood that one skilled in the art may be able to make these compounds by similar methods or by combining other methods known to one skilled in the art. It is also understood that one skilled in the art would be able to make, in a similar manner as described below, other compounds of structure (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described herein.

The following examples are provided for purposes of illustration, not limitation.

EXAMPLES

General Purification Procedures

Method #1: Purification by Acidic Condition
Mobile Phases:
  A—Water with 0.1% TFA
  B—Acetonitrile with 0.1% TFA
Columns:
  A: Phenomenex Luna C18
    21.4×250 mm, 10 µm
    Gradient: 0-100%, flow 25 ml/min
  B: Phenomenex Luna C18
    50×250 mm, 10 µm
    Gradient: 0-100%, flow 45 ml/min
Method #2: Purification by Basic Condition
Mobile Phases:
  A—Water with 0.25 M $NH_4OH$
  B—Acetonitrile with 0.25 M $NH_4OH$
  Column: Phenomemex Gemini-NX 150×21.2 mm, 10 µm C18 110A
  Gradient: 0% B over 20 min, 0-10% B over 70 min, flow 15 ml/min General Procedure Sulfate Salt Swap To a solution of the aminoglycoside salt (0.074 mmol) in $H_2O$ (1 mL) was added 1 M $NH_4OH$ (~400 µL) to adjust the pH to 7-8, followed by $(NH_4)_2SO_4$ (0.22 mmol, 3 eq.). The resulting solution was filtered through a 0.45 µm PVDF filter, and the filtrate was dripped into vigorously stirring MeOH (40 mL). After 20 min the precipitate was collected by centrifugation and dried for 1 h under vacuum. The solid was dissolved in $H_2O$ (1 mL) and precipitated with MeOH (40 mL) a second time. The resulting precipitate was collected by centrifugation, dissolved in $H_2O$ (3 mL) and lyophilized to yield the product as its sulfate salt.

Representative Compounds

Example 1

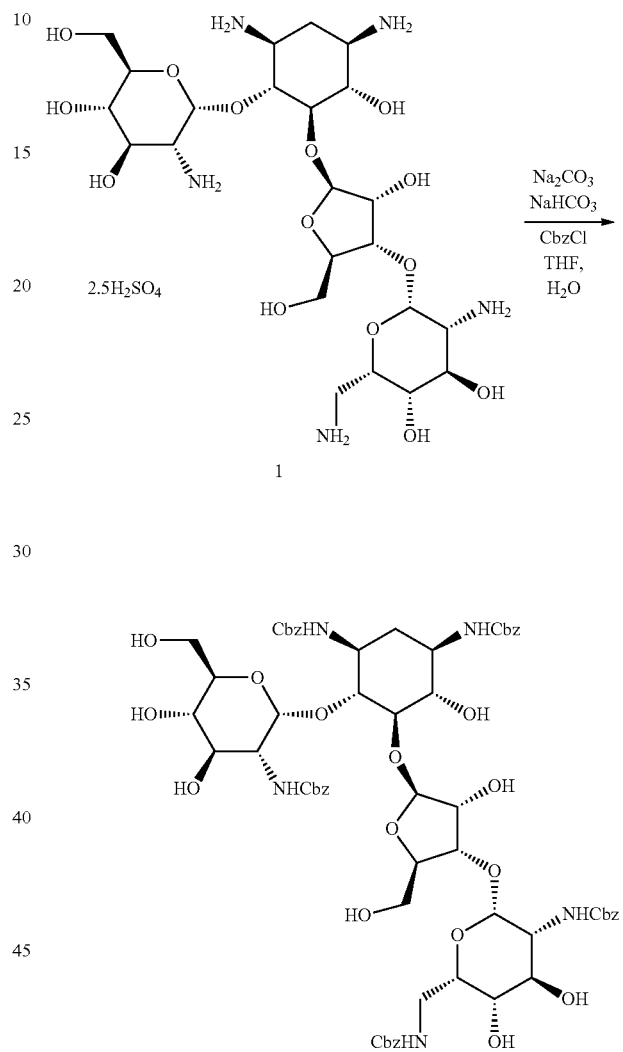

To a stirring solution of paromomycin sulfate 1 (76.0 g, 84 mmol) in $H_2O$ (209 mL) and THF (1084 mL) at 0° C. was added an aqueous solution of sodium carbonate (254 mL, 218 mmol, 0.86 M), followed by the dropwise addition of benzyl chloroformate (120 mL, 840 mmol). $NaHCO_3$ (70.6 g, 840 mmol) was then added and the reaction was stirred for 3 hr. The organic layer was separated and concentrated (to about 800 mL), diluted with EtOAc (400 mL) and dripped into hexane (9 L). The resulting precipitate was collected by filtration to yield 2 (69.85 g, 54.36 mmol, 65%): MS m/z calcd for $C_{63}H_{75}N_5O_{24}$ 1308.5 (M+Na$^+$). found 1308.6.

19

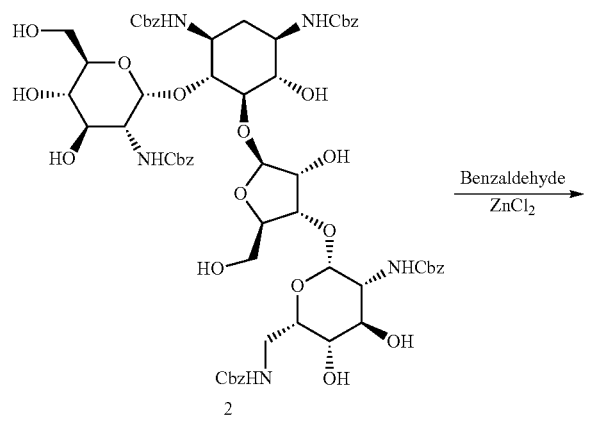

2

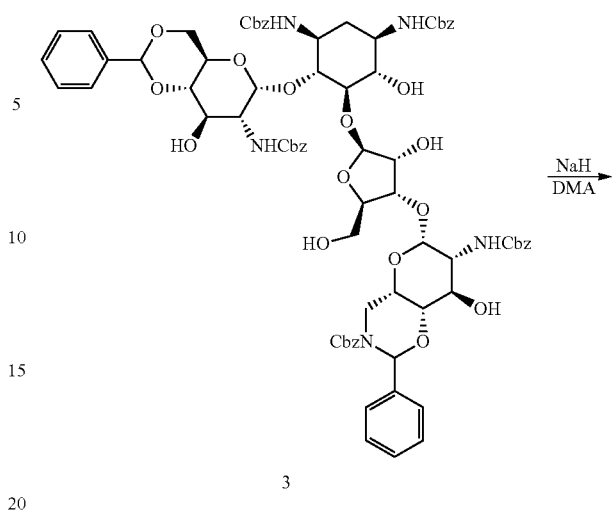

3

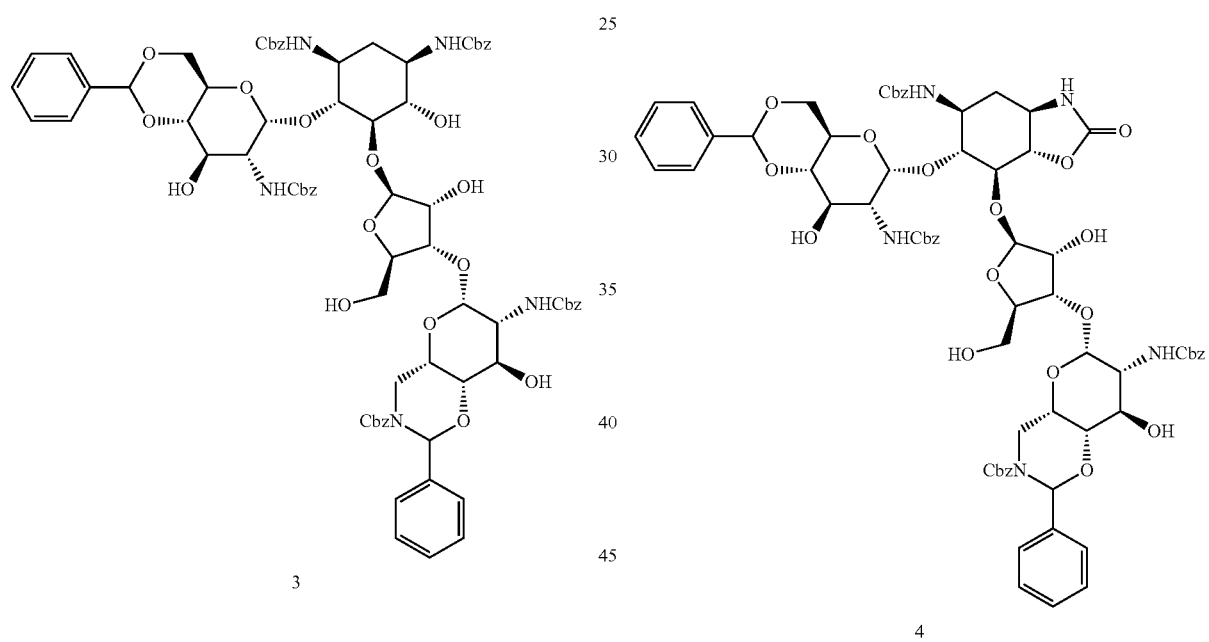

3

4

Zinc chloride (59.2 g, 434 mmol) was dissolved in benzaldehyde (440 mL, 4344 mmol) to give a yellow solution, and the reaction was stirred for 5 min. A solution of 2 (69.85 g, 54.3 mmol) in benzaldehyde (440 mL) was then added and the reaction was stirred for 7 hr. The reaction mixture was diluted with EtOAc (2 L) and washed with 0.1M EDTA disodium salt dihydrate (3×2 L), H$_2$O (2 L), brine (2 L), dried over Na$_2$SO$_4$, concentrated (to about 900 mL) and dripped into Et$_2$O:hexane (1:1, 4 L). The resulting precipitate was collected by filtration and dried under vacuum to yield 3 (93.4 g), which was carried through to the next step without further purification: MS m/z calcd for $C_{77}H_{83}N_5O_{24}$ 1484.5 (M+Na$^+$). found 1484.7.

To a stirring suspension of sodium hydride (dry 95%, 9.64 g, 382 mmol) in DMA (501 mL) at −10° C. was added a solution of 3 (93.0 g, 63.6 mmol) in DMA (500 mL) and the reaction was stirred for 4 hours. The reaction was quenched with acetic acid (100 mL) and stirred for 30 minutes. The reaction mixture was then diluted with EtOAc (2 L), and washed with NaHCO$_3$ (2×2 L), H$_2$O (2×2 L), brine (2 L), dried over Na$_2$SO$_4$, filtered and concentrated to a yellow-brown solid, which was purified by flash chromatography (silica gel, MeOH/DCM) to yield 4 (30.0 g, 22.17 mmol, 35%): MS m/z calcd for $C_{20}H_{75}N_3O_{23}$ 1376.5 (M+Na$^+$). found 1376.7.

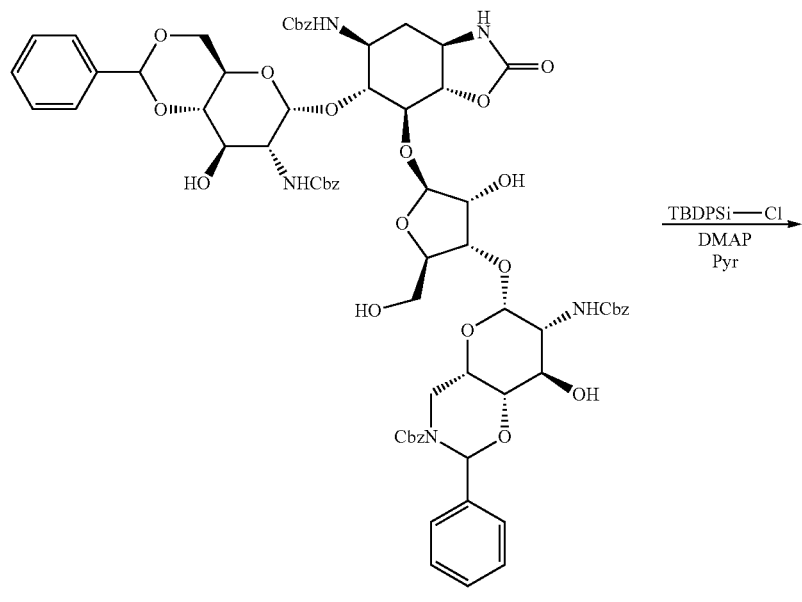

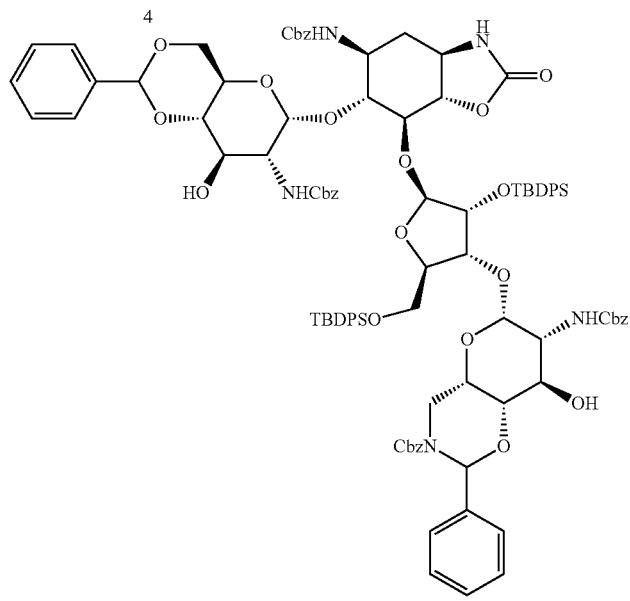

4

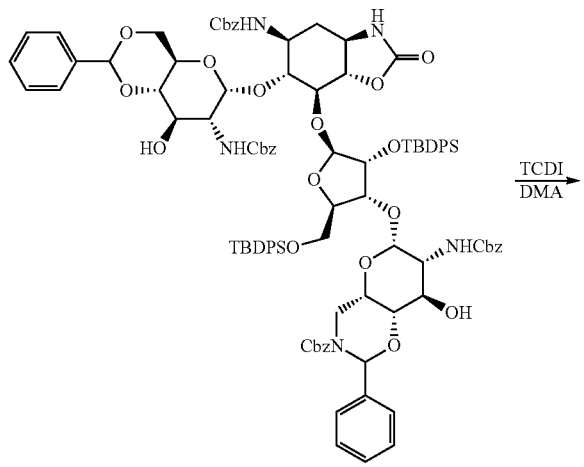

5

To a stirring solution of 4 (30.0 g, 22.15 mmol) in pyridine (201 mL) was added DMAP (2.71 g, 22.15 mmol), followed by TBDPSi—Cl (65.4 mL, 255 mmol) and the reaction was heated at 80° C. for 6 days. The reaction mixture was dripped into $Et_2O$:hexane (1:1, 9 L) and the resulting precipitate was collected by filtration and re-dissolved in THF (130 mL) and MeOH (40 mL). This solution was then dripped into $Et_2O$:hexane (1:1, 9 L) and the resulting precipitate was collected by filtration and dried under vacuum. The white solid was dissolved in ethyl acetate (600 mL), washed with 1M citric acid (2×500 mL), brine (500 mL), $NaHCO_3$ (2×500 mL), brine (500 mL), dried over $Na_2SO_4$, filtered and concentrated to yield 5 (36.45 g, 19.93 mmol, 90%): MS m/z calcd for $C_{102}H_{111}N_5O_{23}Si_2$ 1852.7 (M+Na$^+$). found 1852.8.

5

-continued

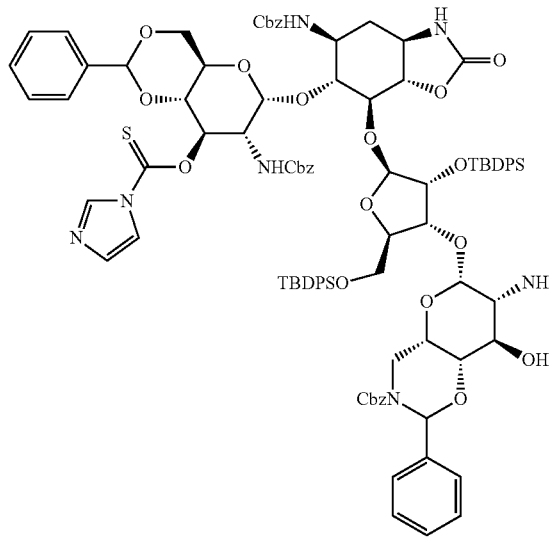

6

To a stirring solution of 5 (5.0 g, 2.73 mmol) in DMA (49.6 mL) was added 1'-thiocarbonyldiimidazole (4.53 g, 25.4 mmol) and the reaction was heated at 40° C. for 18 hours. The reaction was diluted with ethyl acetate (100 mL), washed with 1M citric acid (3×100 mL), brine (3×100 mL), dried over $Na_2SO_4$, filtered and concentrated to an orange foam, which was purified by flash chromatography (silica gel/DCM/MeOH) to yield compound 6 (4.5 g, 2.32 mmol, 85%): MS m/z calcd for $C_{106}H_{113}N_7O_{23}Si_2$ 1962.7 (M+Na$^+$). found 1962.8.

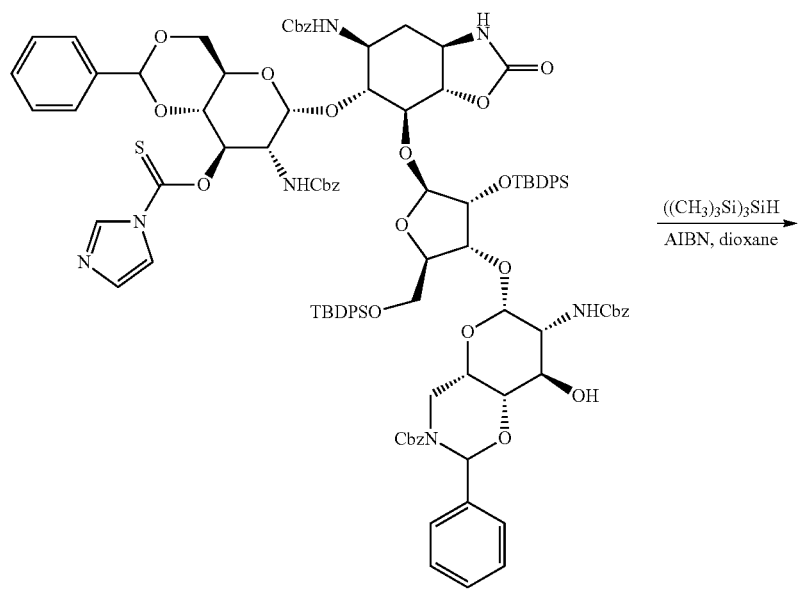

6

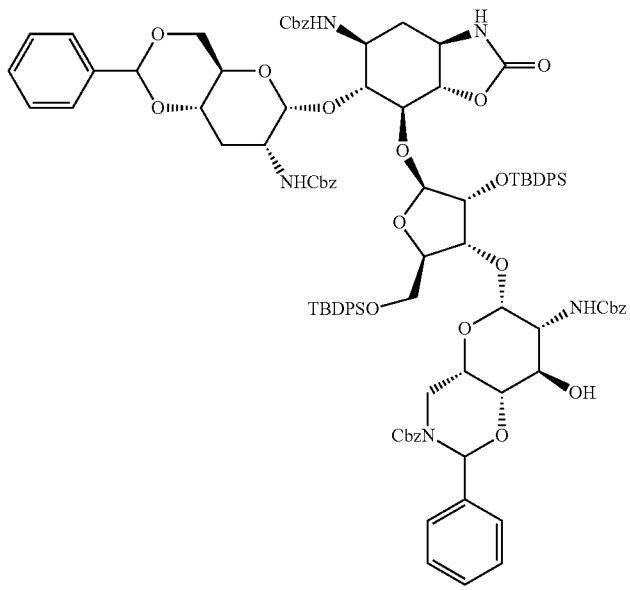

7

To a stirring solution of 6 (1.85 g, 0.953 mmol) in dioxane (68.1 mL) was added tris(trimethylsilyl)silane (0.882 mL, 2.86 mmol), followed by AIBN (0.063 g, 0.381 mmol) and the reaction was heated at 80° C. for 2 hours. The reaction was diluted with ethyl acetate (50 mL), washed with sat. aq. NaHCO$_3$ (50 mL), brine (50 mL), dried over Na$_2$SO$_4$, filtered and concentrated to yield compound 7 (3.0 g), which was carried through to the next step without further purification. MS m/z calcd for C$_{102}$H$_{111}$N$_5$O$_{22}$Si$_2$ 1836.7 (M+Na$^+$). found 1837.0.

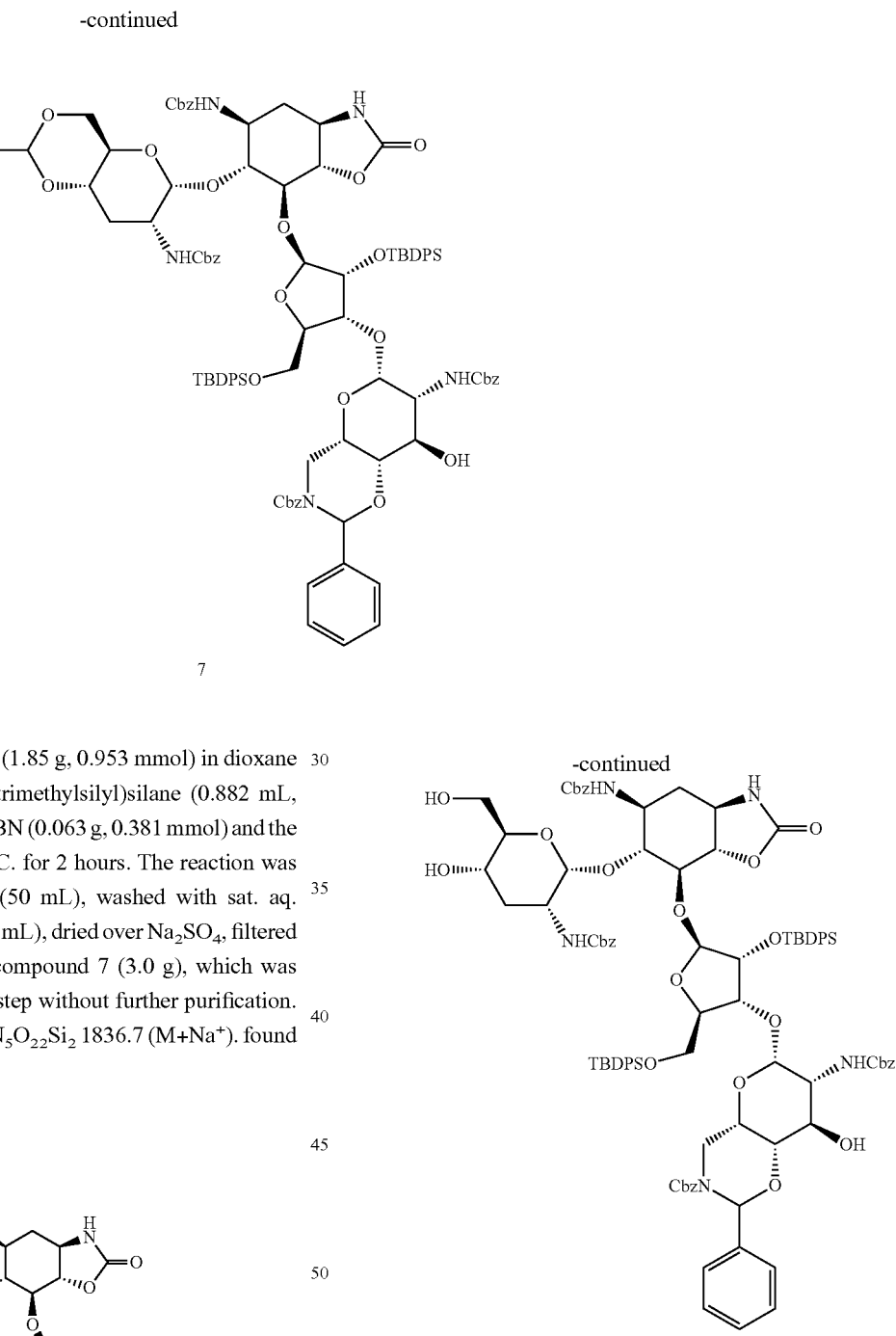

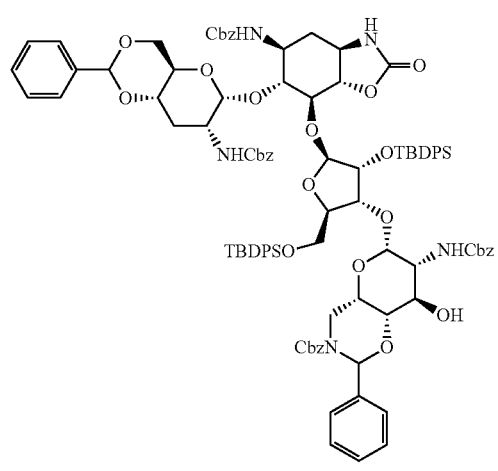

7

To a stirring solution of 7 (3.911 g, 2.155 mmol) in acetic acid (50 mL) was slowly added a solution of TFA (0.385 mL, 5.00 mmol) in water (6.94 mL) and the reaction was heated at 50° C. for 90 minutes. The reaction was cooled to 0° C. and was quenched with DIPEA (1.746 mL, 10.00 mmol). The reaction mixture was then diluted with ethyl acetate (100 mL), washed with water (100 mL), brine (100 mL), sat. aq. NaHCO$_3$ (2×100 mL), brine (100 mL), dried over Na$_2$SO$_4$, filtered and concentrated to a crude solid, which was purified on a 2-inch reverse phase HPLC to yield compound 8 (1.0 g, 0.58 mmol, 27%): MS m/z calcd for C$_{95}$H$_{107}$N$_5$O$_{22}$Si$_2$ 1748.7 (M+Na$^+$). found 1748.8.

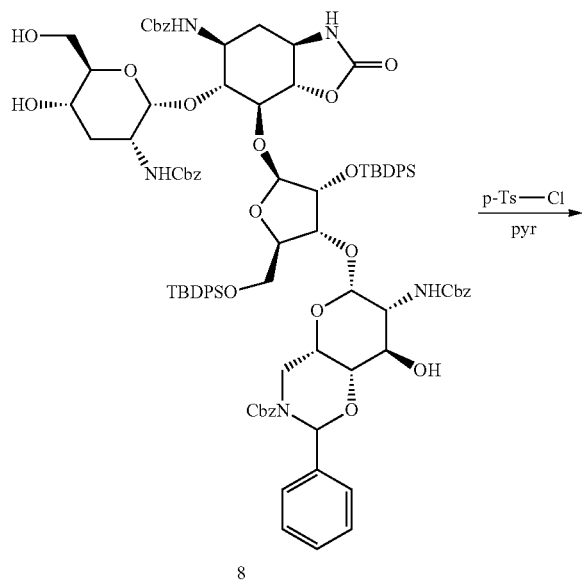

8

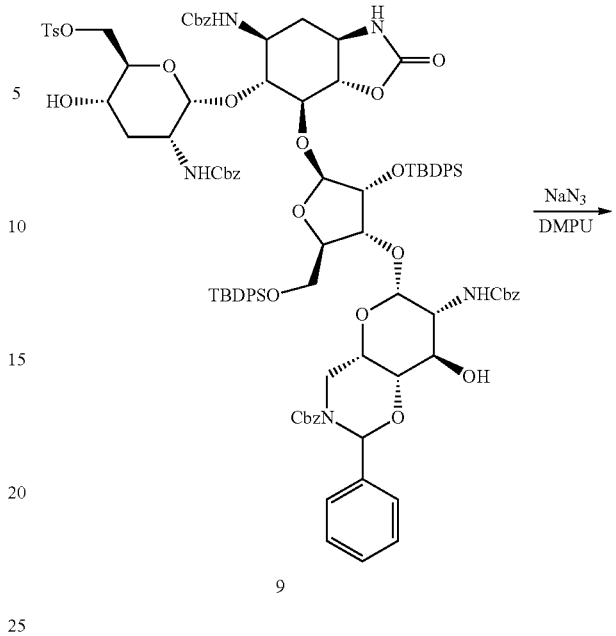

9

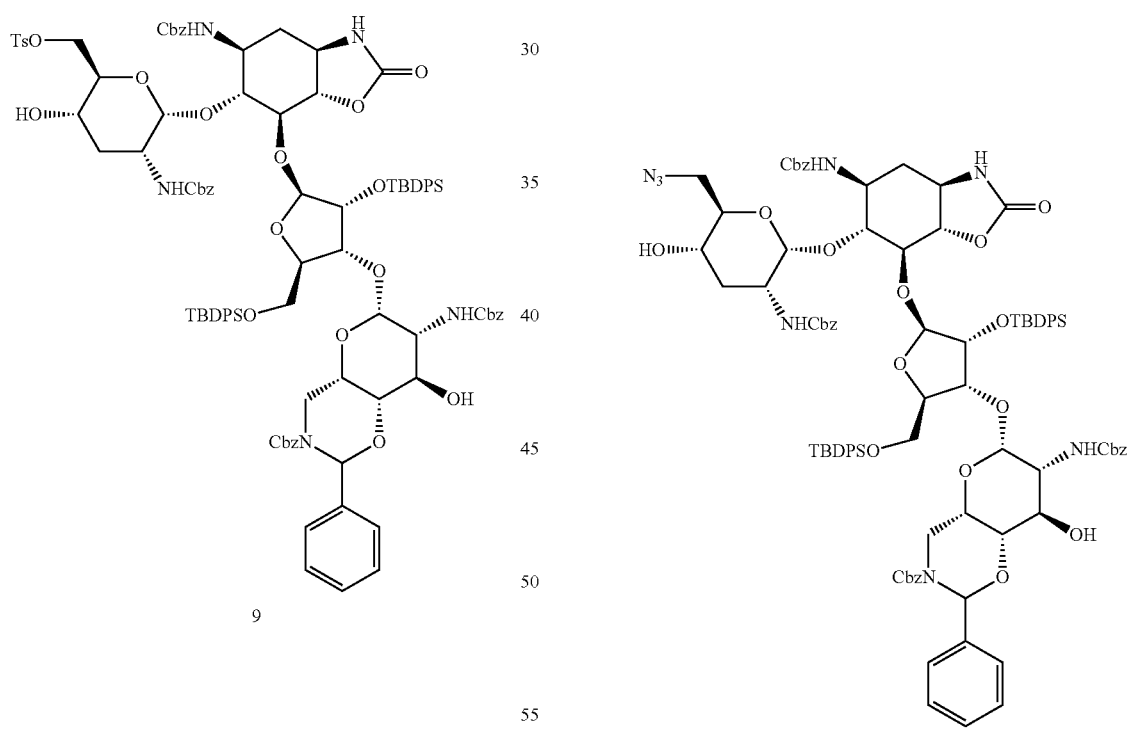

10

To a stirring solution of 8 (1.00 g, 0.58 mmol) in pyridine (19.3 mL) was added p-toluenesulfonyl chloride (0.883 g, 4.64 mmol) and the reaction was stirred for 7 hours. The reaction mixture was diluted with ethyl acetate (50 mL), washed with 1M citric acid (2×50 mL), water (50 mL), brine (50 mL), sat aq. NaHCO$_3$ (2×50 mL), brine (50 mL), dried over Na$_2$SO$_4$, filtered and concentrated to a crude solid, which was purified on a 2-inch reverse phase HPLC column to yield 9 (0.558 g, 0.297 mmol, 57%): MS m/z calcd for C$_{102}$H$_{113}$N$_5$O$_{24}$SSi$_2$ 1902.7 (M+Na$^+$). found 1902.8.

To a stirring solution of 9 (0.5 g, 0.266 mmol) in DMPU (8.8 mL) was added sodium azide (0.172 g, 2.658 mmol) and the reaction was heated at 70° C. for 3 hours. The reaction was diluted with ethyl acetate (50 mL), washed with brine:water (1:1, 50 mL), water (2×50 mL), brine (50 mL), dried over Na$_2$SO$_4$, filtered and concentrated to yield compound 10 (0.480 g, 0.266 mmol): MS m/z calcd for C$_{95}$H$_{106}$N$_8$O$_{21}$Si$_2$ 1773.7 (M+Na$^+$). found 1773.7.

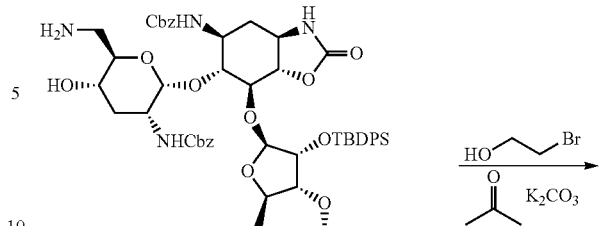

10

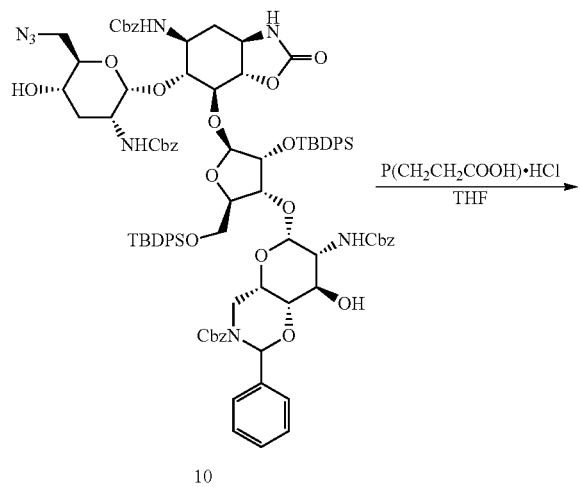

11

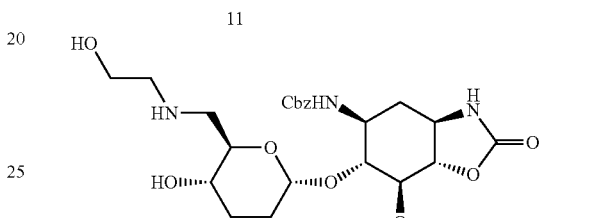

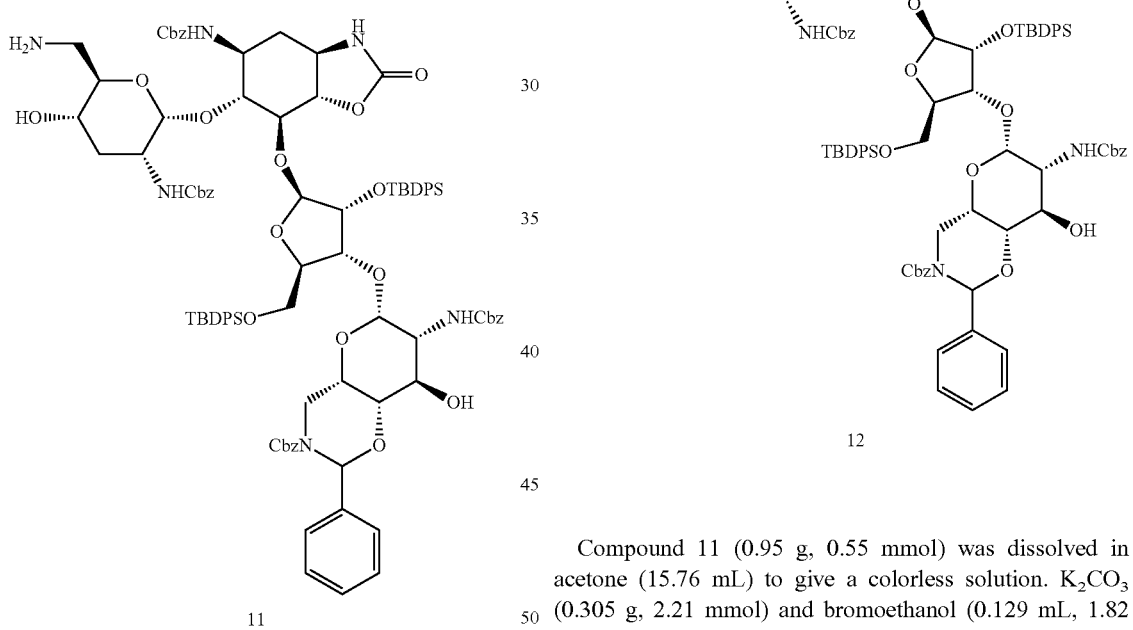

12

Compound 10 (2.73 g, 1.56 mmol) was dissolved in THF (47 mL) to give a yellow solution. DIPEA (4.08 mL, 23.37 mmol) and tris-(2-carboxyethyl)phosphine hydrochloride (2.23 g, 7.79 mmol) were then added and the reaction was stirred for 24 hours. The reaction was diluted with ethyl acetate (100 mL), washed with brine (100 mL), NaHCO$_3$ (2×100 mL), brine (100 mL), dried over Na$_2$SO$_4$, filtered, and concentrated to a white solid, which was purified by reverse phase HPLC to yield 11 (0.95 g, 0.55 mmol, 35%): MS: m/z calcd for C$_{95}$H$_{108}$N$_6$O$_{21}$Si$_2$ 1725.7 (M+H$^+$). found 1725.5.

Compound 11 (0.95 g, 0.55 mmol) was dissolved in acetone (15.76 mL) to give a colorless solution. K$_2$CO$_3$ (0.305 g, 2.21 mmol) and bromoethanol (0.129 mL, 1.82 mmol) were then added and the reaction was heated at 35° C. for 3 days. Additional K$_2$CO$_3$ (0.305 g, 2.21 mmol) and bromoethanol (0.129 mL, 1.82 mmol) were added and the reaction was heated at 35° C. for 1 day. Additional K$_2$CO$_3$ (0.305 g, 2.21 mmol) and bromoethanol (0.387 mL, 5.46 mmol) were added and the reaction was heated at 35° C. for 2 days. Additional K$_2$CO$_3$ (0.305 g, 2.21 mmol) and bromoethanol (0.129 mL, 1.82 mmol) were added and the reaction was heated at 35° C. for one day. Finally, the reaction was diluted with ethyl acetate (100 mL), washed with water (100 mL) and brine (100 mL), dried over Na$_2$SO$_4$, filtered, and then concentrated to dryness to yield compound 12 (1.06 g, 0.60 mmol), which was carried through to the next step without further purification. MS: m/z calcd for C$_{97}$H$_{112}$N$_6$O$_{22}$Si$_2$ 1769.7 (M+H$^+$). found 1769.6.

31

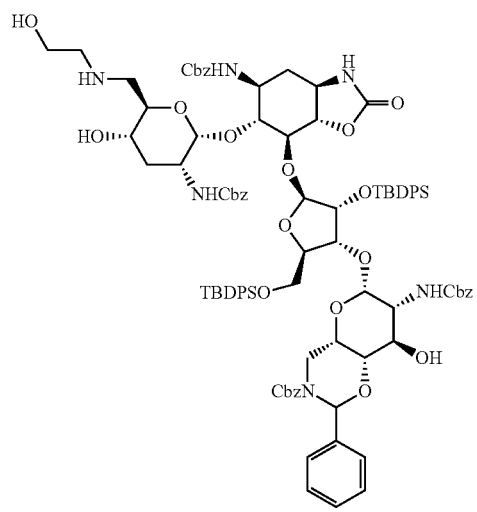

12

32

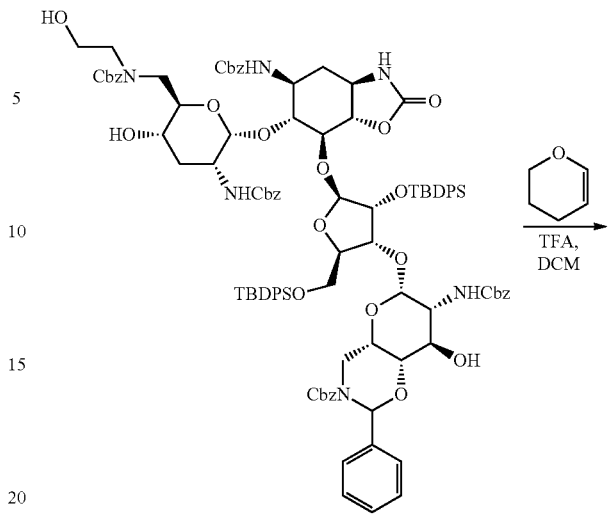

13

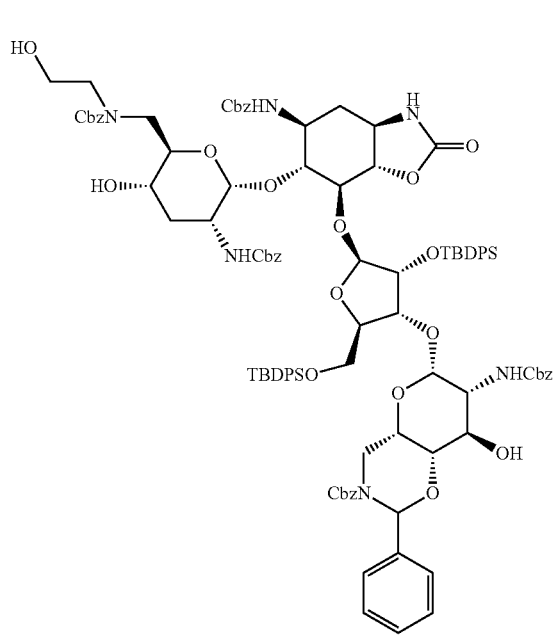

13

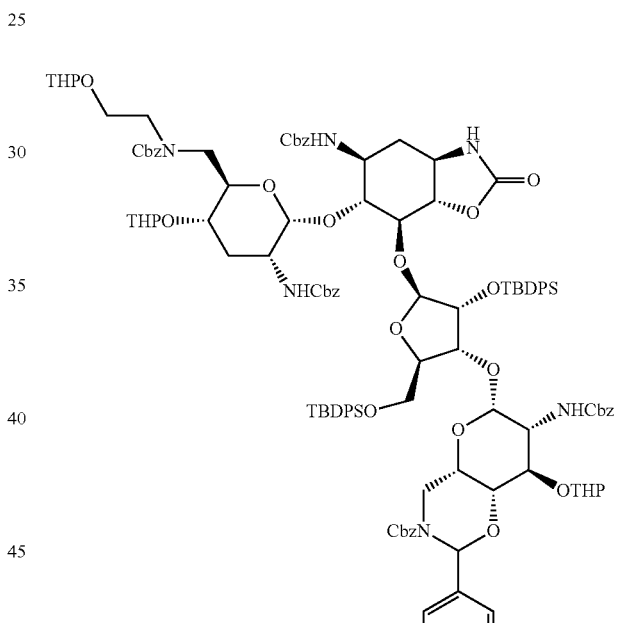

14

Compound 12 (2.84 g, 1.61 mmol) was dissolved in acetonitrile (21.4 mL) and water (5.36 mL) to give a colorless solution. Cbz-O-Suc (0.88 g, 3.53 mmol) and DIPEA (1.12 mL, 6.43 mmol) were then added and the reaction was stirred for 18 hours. The reaction was diluted with ethyl acetate (100 mL), washed with 1M citric acid (100 mL), brine (100 mL), NaHCO$_3$ (100 mL), brine (100 mL), dried over Na$_2$SO$_4$, filtered and concentrated to a white foam, which was purified by reverse phase HPLC to yield compound 13 (1.27 g, 0.67 mmol, 42%): MS: m/z calcd for C$_{105}$H$_{118}$N$_6$O$_{24}$Si$_2$ 1925.8 (M+Na$^+$). found 1925.6.

Compound 13 (1.44 g, 0.76 mmol) was dissolved in DCM (30 mL) to give a colorless solution. DHP (0.48 mL, 5.29 mmol) and TFA (0.058 mL, 0.756 mmol) were then added and the reaction was stirred for 4 hours. The reaction was diluted with DCM (100 mL), washed with NaHCO$_3$ (100 mL), brine (100 ml), dried over Na$_2$SO$_4$, filtered and concentrated to dryness to yield compound 14 (1.59 g, 0.74 mmol), which was carried through to the next step without further purification.

33

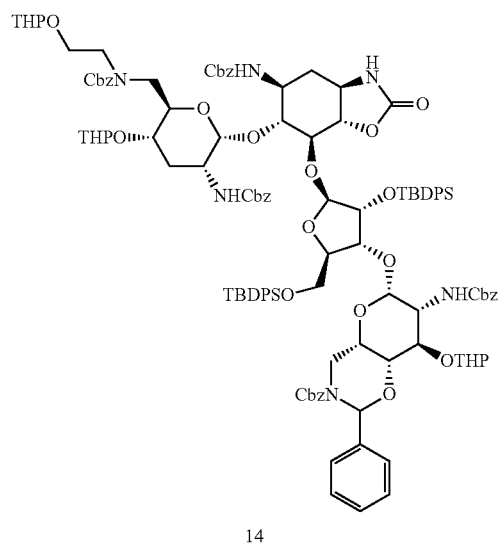

14

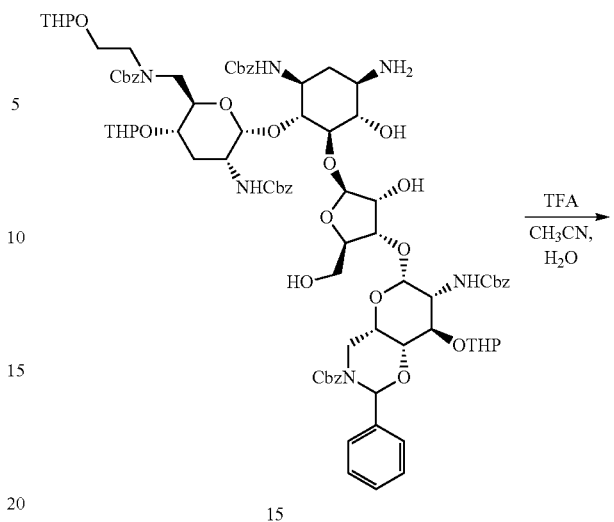

15

34

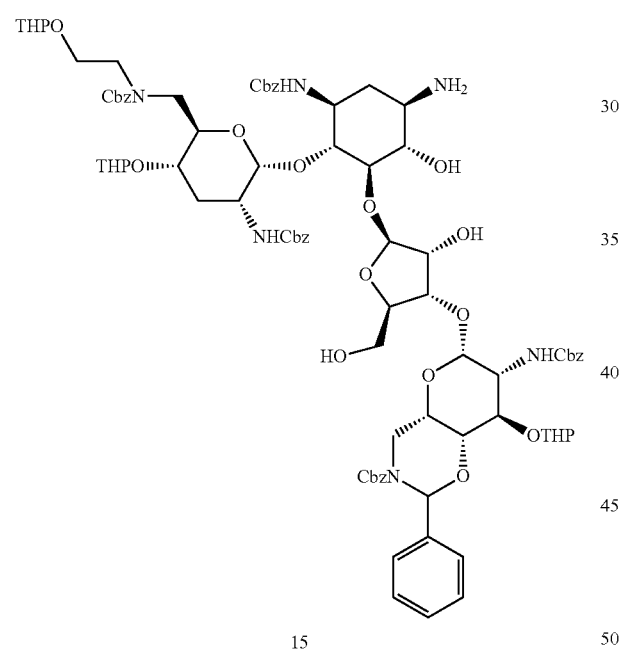

15

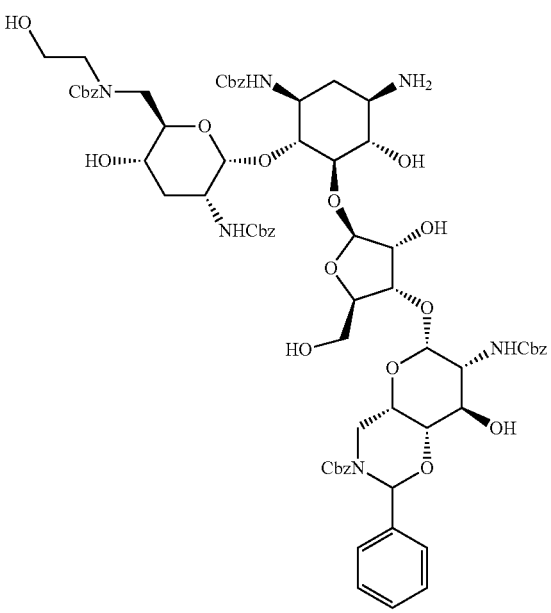

16

Compound 14 (1.0 g, 0.50 mmol) was dissolved in 1.0 M TBAF in THF (5.53 mL, 5.53 mmol) and the reaction was heated at 50° C. for 15 hours. The reaction was then diluted with ethyl acetate (100 mL), washed with NaHCO$_3$ (100 mL), brine (100 mL), dried over Na$_2$SO$_4$, filtered and concentrated to dryness to yield compound 15 (0.93 g), which was carried through to the next step without further purification. LCMS samples were made by diluting with 1:1 acetonitrile:water with 0.1% TFA followed by aging for one hour to remove the THP groups. MS: m/z calcd for C$_{72}$H$_{84}$N$_6$O$_{23}$ 1423.6 (M+Na$^+$). found 1423.4.

Compound 15 (0.933 g, 0.628 mmol) was dissolved in acetonitrile (1.04 mL) to give a yellow solution. The reaction mixture was then diluted with TFA (0.104 mL) and water (1.04 mL), and was stirred for 4 hours. The crude reaction was purified by reverse phase HPLC to yield compound 16 (0.33 g, 0.235 mmol, 24%): MS: m/z calcd for C$_{72}$H$_{84}$N$_6$O$_{23}$ 1423.6 (M+Na$^+$). found 1423.4.

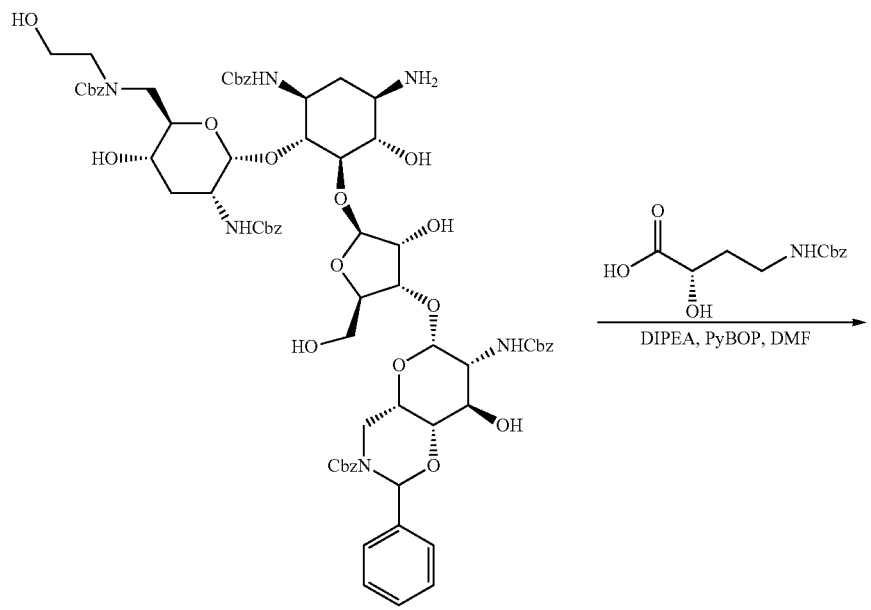

16

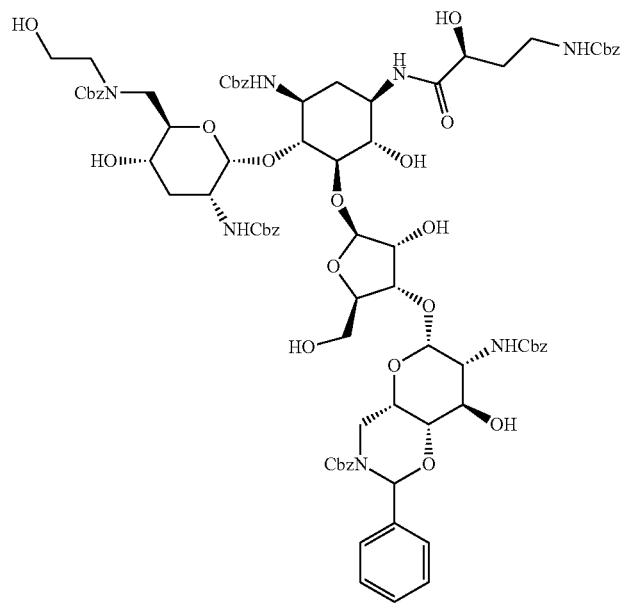

17

To a stirring solution of 16 (25 mg, 0.018 mmol) in DMF (0.3 mL) at 0° C. was added N-Cbz-2(S)-hydroxy-4-aminobutyric acid (5 mg, 0.020 mmol), followed by PyBOP (8 mg, 0.021 mmol) and DIPEA (7.8 μL, 0.045 mmol) and the reaction was stirred for 1 hr with warming to room temp until complete (by LC-MS). The reaction mixture was diluted with DMF (0.5 mL) and was loaded directly onto a 1-inch reverse phase HPLC column to yield 17 (24 mg, 0.015 mmol, 83.3%): MS: m/z calcd for $C_{84}H_{97}N_7O_{27}$ 1658.6 (M+Na$^+$). found 1658.5.

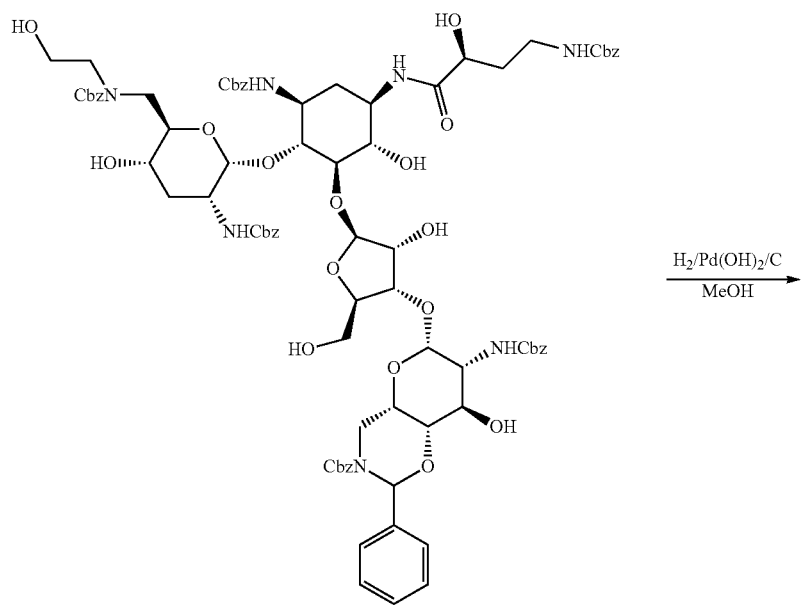

17

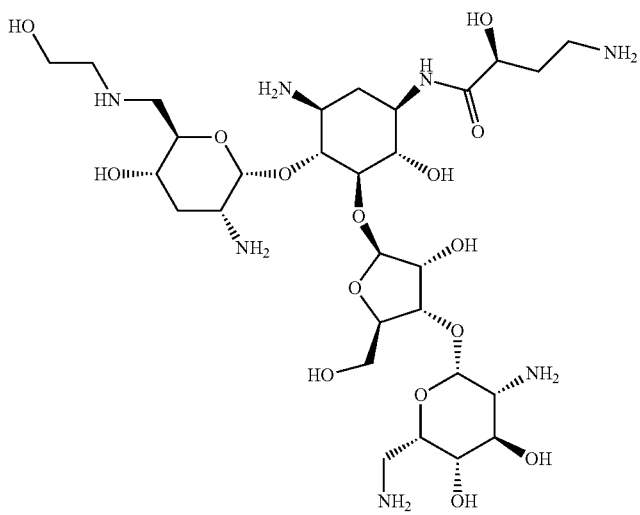

18

To a stirring solution of 17 (24 mg, 0.015 mmol) in MeOH (3 mL) was added 20% Pd(OH)$_2$/C (21 mg) followed by TFA (0.014 mL, 0.179 mmol) and the reaction was stirred under a hydrogen atmosphere for 18 hr. Additional Pd(OH)$_2$/C (21 mg) was added and the reaction was stirred under a hydrogen atmosphere for 7 hours. The reaction was filtered through a 0.45 μm PVDF filter, diluted with water and lyophilized to yield 18 as its TFA salt, which was purified by reverse phase HPLC (Method 2) and converted to its sulfate salt (2 mg, 0.002 mmol, 13.3%): MS m/z calcd for $C_{29}H_{57}N_7O_{15}$ (M+H)$^+$744.8. found 744.4; CLND 97.9%.

Example 2

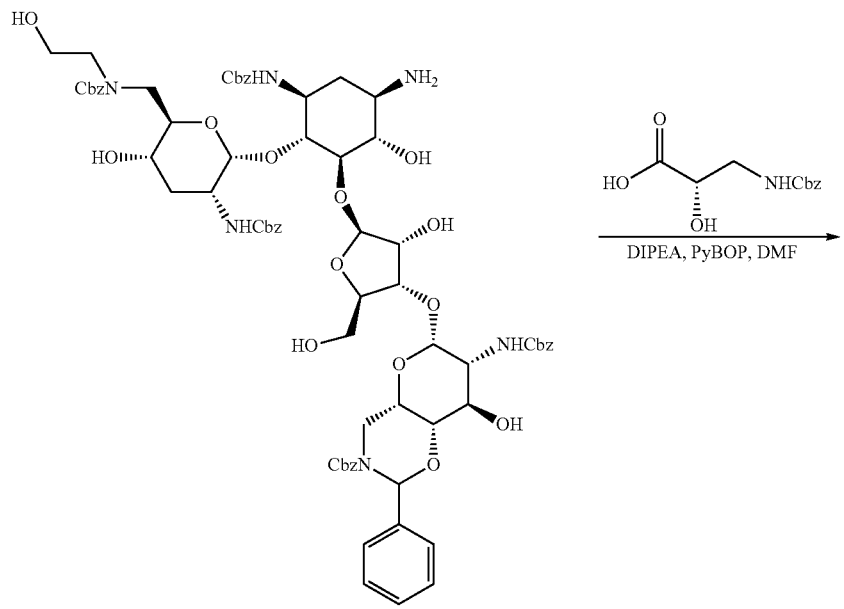

16

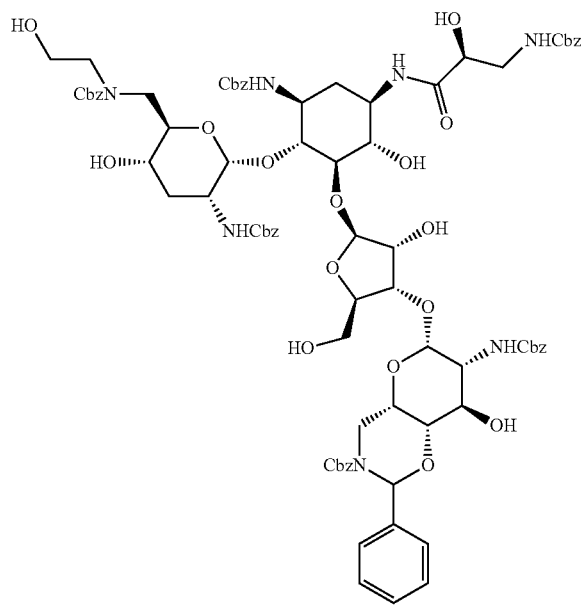

19

To a stirring solution of 16 (275 mg, 0.268 mmol) in DMF (3.5 mL) at 0° C. was added N-Cbz-2(S)-hydroxy-3-aminopropionic acid (70 mg, 0.294 mmol), followed by PyBOP (167 mg, 0.321 mmol) and DIPEA (0.122 mL, 0.696 mmol) and the reaction was stirred with warming to room temp until complete (by LC-MS). The reaction mixture was diluted with AcOH (1 mL) and was loaded onto a 2-inch reverse phase HPLC column to yield 19 (337 mg, 0.208 mmol, 77.6%): MS: m/z calcd for $C_{83}H_{95}N_7O_{27}$ 1645.7 (M+Na$^+$). found 1645.7.

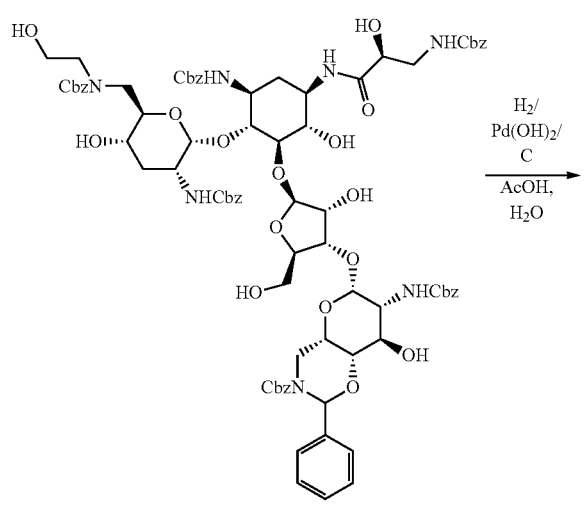

19

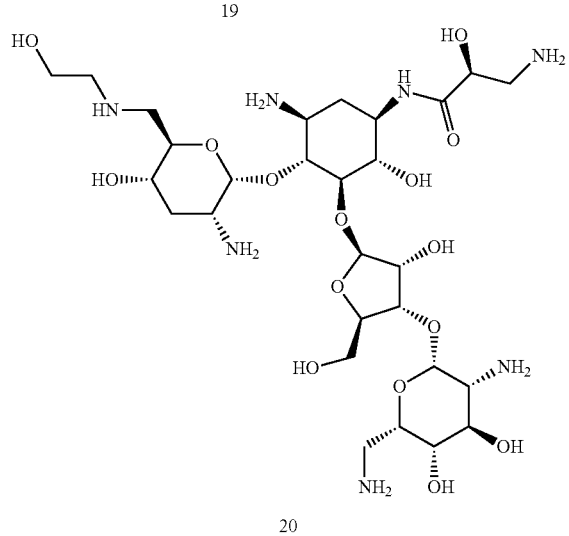

20

To a stirring solution of 19 (335 mg, 0.206 mmol) in AcOH (8.3 mL) and water (2 mL) was added Pd(OH)$_2$/C (348 mg) and the reaction was stirred under a hydrogen atmosphere for 2 hr. Additional Pd(OH)$_2$/C was added and the reaction was stirred under a hydrogen atmosphere for 2 hours. The reaction was filtered through a 0.45 μm PVDF filter, diluted with water (100 mL) and lyophilized to yield 20 as its acetate salt, which was purified by reverse phase HPLC (Method 2) and converted to its sulfate salt (169 mg, 0.165 mmol, 80.1%): MS m/z calcd for $C_{28}H_{55}N_7O_{15}$ (M+H)$^+$ 730.8. found 730.3; CLND 100%.

MIC ASSAY PROTOCOL

Minimum inhibitory concentrations (MIC) were determined by reference Clinical and Laboratory Standards Institute (CLSI) broth microdilution methods per M7-A7 [2006]. Quality control ranges utilizing *E. coli* ATCC 25922, *P. aeruginosa* ATCC 27853 and *S. aureus* ATCC 29213, and interpretive criteria for comparator agents were as published in CLSI M100-S17 [2007]. Briefly, serial two-fold dilutions of the test compounds were prepared at 2× concentration in Mueller Hinton Broth. The compound dilutions were mixed in 96-well assay plates in a 1:1 ratio with bacterial inoculum. The inoculum was prepared by suspension of a colony from an agar plate that was prepared the previous day. Bacteria were suspended in sterile saline and added to each assay plate to obtain a final concentration of 5×10$^5$ CFU/mL. The plates were incubated at 35 C for 20 hours in ambient air. The MIC was determined to be the lowest concentration of the test compound that resulted in no visible bacterial growth as compared to untreated control. Data for certain representative compounds is shown in Tables 1 and 2 below.

The MIC panel presented in Table 1 contains 27 isolates of *Pseudomonas aeruginosa*: strains 1-22 are clinical isolates from around the world collected between 2004-2007 which contain representative resistance mechanisms commonly found in *Pseudomonas*, such as the AAC(6')-I, AAC(6')-II, APH(3')-IIb, ANT(2")-I, and perm/efflux; strains 23-27 are susceptible.

TABLE 1

| clinical strain | MIC (μg/mL) | | | | | |
|---|---|---|---|---|---|---|
| | AMK | GEN | TOB | Neo B | Compound 18 | Compound 20 |
| 1 | E | D | E | E | A | A |
| 2 | E | E | D | D | A | A |
| 3 | E | E | E | E | B | B |
| 4 | E | E | E | E | B | B |
| 5 | E | E | E | E | B | B |
| 6 | C | E | E | D | B | B |
| 7 | B | E | E | C | A | A |
| 8 | D | E | E | E | C | B |
| 9 | C | E | E | D | B | A |
| 10 | D | E | E | E | C | B |
| 11 | A | D | C | B | A | A |
| 12 | A | E | E | E | B | A |
| 13 | B | E | E | E | D | C |
| 14 | B | E | E | E | B | A |
| 15 | C | E | E | E | B | B |
| 16 | E | E | E | E | B | A |
| 17 | E | E | E | C | B | B |
| 18 | E | E | E | E | B | B |
| 19 | E | E | E | E | D | D |
| 20 | E | C | B | E | D | D |
| 21 | D | C | A | E | C | B |
| 22 | D | B | A | E | B | B |
| 23 | B | A | A | B | A | A |
| 24 | B | B | A | B | A | A |
| 25 | B | A | A | B | A | A |
| 26 | B | A | A | C | A | A |
| 27 | A | A | B | B | A | A |

** MIC Key:
MIC's of 1.0 μg/mL or less = A
MIC's of greater than 1.0 μg/mL and lower than 8 μg/mL = B
MIC's greater than or equal to 8 μg/mL and lower than 16.0 μg/mL = C
MIC's greater than or equal to 16.0 μg/mL and lower than 32 μg/mL = D
MIC's greater than or equal to 32.0 μg/mL = E
AMK = amikacin
GEN = gentamicin
TOB = tobramycin
Neo B = neomycin B The MIC panel presented in Table 2 contains 29 isolates of *Acinetobacter baumannii*: strains 1-24 are clinical isolates from around the world collected between 2004-2007 which contain representative resistance mechanisms commonly found in *Acinetobacter baumannii*, such as AAC(3)-I and II, AAC(6')-I, ANT(2")-I, APH(3')-VI, and perm/efflux; strains 25-29 are susceptible.

TABLE 2

| clinical strain | AMK | GEN | TOB | Compound 18 | Compound 20 |
|---|---|---|---|---|---|
| 1 | E | E | E | B | B |
| 2 | E | E | E | C | B |
| 3 | C | C | E | B | A |
| 4 | D | E | E | D | D |
| 5 | E | E | E | B | A |
| 6 | E | E | E | B | B |
| 7 | E | E | B | A | A |
| 8 | E | E | E | B | A |
| 9 | B | E | E | A | A |
| 10 | B | E | E | B | B |
| 11 | E | E | E | A | A |
| 12 | E | E | D | A | A |
| 13 | E | A | A | A | A |
| 14 | E | B | A | B | A |
| 15 | E | A | A | A | A |
| 16 | E | B | B | B | B |
| 17 | E | E | A | B | B |
| 18 | E | E | B | C | B |
| 19 | B | B | A | B | B |
| 20 | B | C | B | C | B |
| 21 | E | E | E | A | A |
| 22 | E | E | E | D | C |
| 23 | E | E | E | A | A |
| 24 | E | E | E | D | B |
| 25 | A | A | A | A | A |
| 26 | B | A | A | B | A |
| 27 | B | A | A | A | A |
| 28 | B | A | A | A | A |
| 29 | A | A | A | A | A |

** MIC Key:
MIC's of 1.0 μg/mL or less = A
MIC's of greater than 1.0 μg/mL and lower than 8 μg/mL = B
MIC's greater than or equal to 8 μg/mL and lower than 16.0 μg/mL = C
MIC's greater than or equal to 16.0 μg/mL and lower than 32 μg/mL = D
MIC's greater than or equal to 32.0 μg/mL = E
AMK = amikacin
GEN = gentamicin
TOB = tobramycin

14-DAY RAT TOXICOLOGY PROTOCOL

The objective of this study design was to identify and compare the relative potential for target organ(s) toxicity, particularly the nephrotoxicity, of Compound 20 to that of the comparator aminoglycoside Gentamicin. The study design utilized once-daily subcutaneous injection administration to the rat for 14 days and assessment of reversibility of any changes following a 28-day recovery period.

Compound 20 and control aminoglycoside Gentamicin were administered once-daily by subcutaneous injection administration to 54 rats (27 male and 27 female) for 14 consecutive days as described in Table 3 below.

TABLE 3

| Group Numbers | Group Designation | Dose Level (mg/kg/day) | Dose Conc. (mg/mL) | Number of Main Rats Male | Number of Main Rats Female | Number of Recovery Rats Male | Number of Recovery Rats Female |
|---|---|---|---|---|---|---|---|
| 1 | Control | 0 | 0 | 3 | 3 | 2 | 2 |
| 2 | Gentamicin (Low Dose) | 10 | 10 | 3 | 3 | — | — |
| 3 | Gentamicin (Mid Dose) | 30 | 30 | 3 | 3 | 2 | 2 |
| 4 | Gentamicin (High Dose) | 100 | 100 | 3 | 3 | — | — |
| 5 | Compound 20 (Low Dose) | 10 | 10 | 3 | 3 | — | — |
| 6 | Compound 20 (Mid Dose) | 30 | 30 | 3 | 3 | 2 | 2 |
| 7 | Compound 20 (High Dose) | 100 | 100 | 3 | 3 | — | — |

The dose volume administered to each animal was 1 mL/kg.

The administration of the control aminoglycoside Gentamicin via subcutaneous administration in this model at dose levels of 10, 30 or 100 mg/kg/day to the Sprague-Dawley rat resulted in mortality and morbidity at 100 mg/kg/day due to nephrotoxicity. No statistically significant change was observed in the kidney function readouts serum creatinine and blood urea nitrogen (BUN) for Gentamicin at the low dose level (10 mg/kg/day), while a statistically significant increase in serum creatinine and BUN was observed at the mid and high dose levels (30 mg/kg/day and 100 mg/kg/day). Macroscopic and microscopic changes in the kidneys were observed at all dose levels of gentamicin in this model.

The administration of Compound 20 via subcutaneous administration in this model over a period of 14 days at dose levels of 10, 30 or 100 mg/kg/day to the Sprague-Dawley rat, did not result in mortality at any dose. No statistically significant changes were observed in serum creatinine and BUN for Compound 20 at the 10 mg/kg/day dose, nor any significant macroscopic or microscopic changes to the kidneys.

All of the U.S. patents, U.S. patent application publications, U.S. patent applications, foreign patents, foreign patent applications and non-patent publications referred to in this specification are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A pharmaceutical composition comprising a pharmaceutically acceptable carrier, diluent or excipient and a compound having the following structure (I):

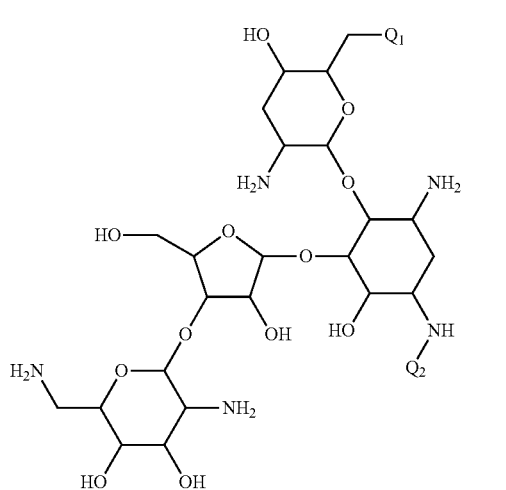

(I)

or a stereoisomer or pharmaceutically acceptable salt thereof, wherein:

$Q_1$ is —$NHR_1$;
Q2 is

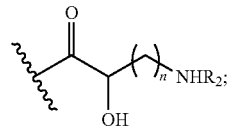

$R_1$ is $C_2$-$C_6$ alkyl substituted with one or two hydroxyl groups;
$R_2$ is hydrogen or $C_1$-$C_6$ alkyl optionally substituted with one or more halogen, hydroxyl or amino; and
n is an integer from 1 to 4.

2. A pharmaceutical composition according to claim 1, wherein $R_1$ is $C_2$-$C_6$ alkyl substituted with one hydroxyl group.

3. A pharmaceutical composition according to claim 2, wherein $R_1$ is —$(CH_2)_m OH$, wherein m is an integer from 2 to 6.

4. A pharmaceutical composition according to claim 3, wherein $R_1$ is —$(CH_2)_2 OH$ or —$(CH_2)_3 OH$.

5. A pharmaceutical composition according to claim 4, wherein $R_1$ is —$(CH_2)_2 OH$.

6. A pharmaceutical composition according to claim 2, wherein $R_1$ is —$(CH_2)_p CH(CH_3)OH$, wherein p is an integer from 1 to 4.

7. A pharmaceutical composition according to claim 6, wherein $R_1$ is —$CH_2 CH(CH_3)OH$ or —$(CH_2)_2 CH(CH_3)OH$.

8. A pharmaceutical composition according to claim 1, wherein $R_1$ is $C_2$-$C_6$ alkyl substituted with two hydroxyl groups.

9. A pharmaceutical composition according to claim 8, wherein $R_1$ is —$CH_2 CH(OH)(CH_2)_q OH$ wherein q is an integer from 1 to 4.

10. A pharmaceutical composition according to claim 9, wherein $R_1$ is —$CH_2 CH(OH)CH_2 OH$ or —$CH_2 CH(OH)(CH_2)_2 OH$.

11. A pharmaceutical composition according to claim 8, wherein $R_1$ is —$(CH_2)_r CH(CH_2 OH)_2$ wherein r is 0 or an integer from 1 to 3.

12. A pharmaceutical composition according to claim 11, wherein $R_1$ is —$CH_2 CH(CH_2 OH)_2$ or —$CH(CH_2 OH)_2$.

13. A pharmaceutical composition according to claim 12, wherein $R_2$ is hydrogen.

14. A pharmaceutical composition according to claim 13, wherein $Q_2$ is:

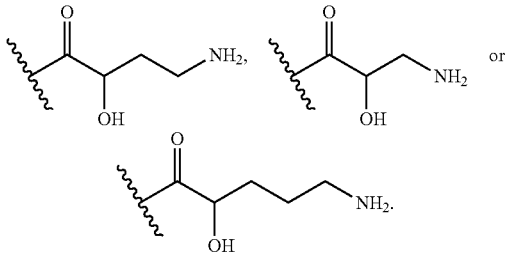

15. A pharmaceutical composition according to claim 14, wherein $Q_2$ is:

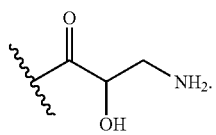 [SMILES: *C(=O)C(O)CN]

16. A pharmaceutical composition according to claim 14, wherein $Q_2$ is:

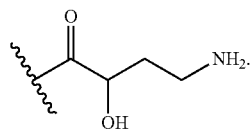 [SMILES: *C(=O)C(O)CCN]

17. A pharmaceutical composition according to claim 1, wherein said compound has the configuration:

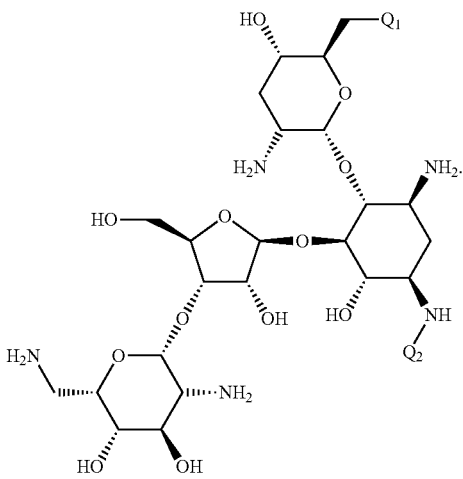

18. A pharmaceutical composition according to claim 1, wherein said compound is:

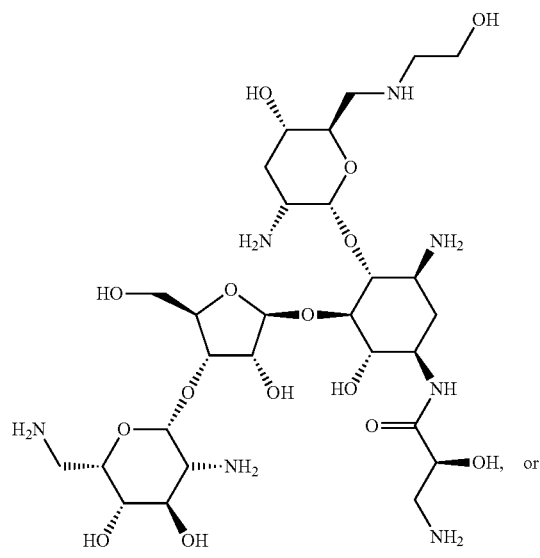

or

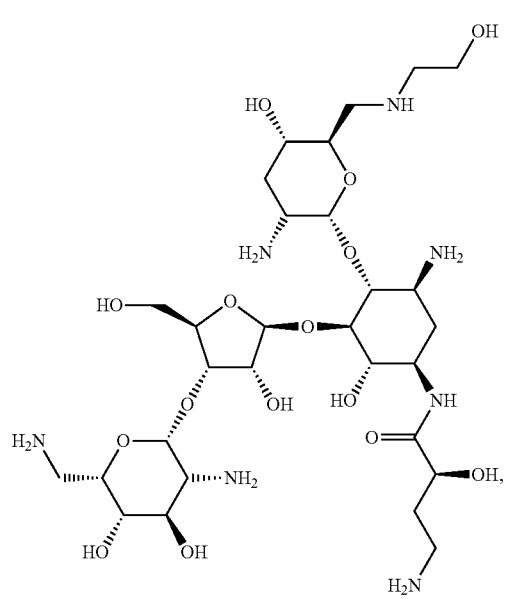

or a pharmaceutically acceptable salt thereof.

19. A pharmaceutical composition according to claim 18, wherein the compound is:

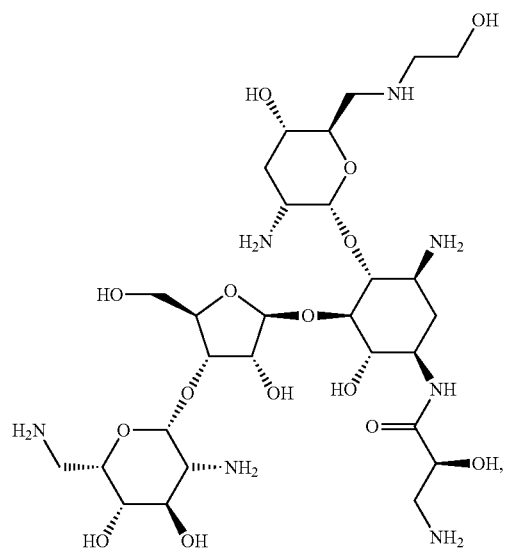

or a pharmaceutically acceptable salt thereof.

20. A pharmaceutical composition according to claim 18, wherein the compound is:

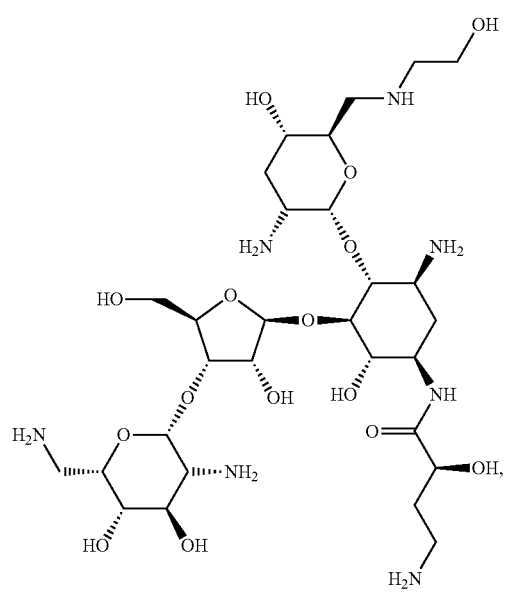

or a pharmaceutically acceptable salt thereof.

* * * * *